US012781254B2

(12) United States Patent
Chen et al.

(10) Patent No.: US 12,781,254 B2
(45) Date of Patent: Nov. 3, 2026

(54) METHOD FOR PREPARING TARGET POLYPEPTIDE BY MEANS OF RECOMBINATION AND SERIES CONNECTION OF FUSED PROTEINS

(71) Applicant: PEG-BIO BIOPHARM CO., LTD. (CHONGQING), Chongqing (CN)

(72) Inventors: Qing Chen, Chongqing (CN); Xin Zeng, Chongqing (CN); Yongliang Peng, Chongqing (CN); Xiaolan Qin, Chongqing (CN); Hui Yang, Chongqing (CN); Kai Fan, Chongqing (CN)

(73) Assignee: PEG-BIO BIOPHARM CO., LTD. (CHONGQING), Chongqing (CN)

( * ) Notice: Subject to any disclaimer, the term of this patent is extended or adjusted under 35 U.S.C. 154(b) by 1063 days.

(21) Appl. No.: 17/558,767

(22) Filed: Dec. 22, 2021

(65) Prior Publication Data

US 2022/0195004 A1 Jun. 23, 2022

Related U.S. Application Data

(63) Continuation of application No. PCT/CN2020/097058, filed on Jun. 19, 2020.

(30) Foreign Application Priority Data

Jun. 26, 2019 (CN) ......................... 201910563692.3

(51) Int. Cl.
*C12P 21/06* (2006.01)
*C07K 14/605* (2006.01)

(52) U.S. Cl.
CPC ............ *C12P 21/06* (2013.01); *C07K 14/605* (2013.01); *C07K 2319/01* (2013.01); *C07K 2319/20* (2013.01); *C07K 2319/50* (2013.01)

(58) Field of Classification Search
CPC ................... C12P 21/06; C07K 14/605; C07K 2319/01; C07K 2319/20; C07K 2319/50; C07K 2319/21; C12R 2001/19; C12N 15/62; C12N 15/70; C12Y 304/21061; C12Y 304/22
See application file for complete search history.

(56) References Cited

U.S. PATENT DOCUMENTS

| | | | | |
|---|---|---|---|---|
| 5,891,671 | A * | 4/1999 | Suzuki | C07K 14/585 435/325 |
| 6,500,645 | B1 * | 12/2002 | Kjeldsen | C12N 15/67 435/254.11 |
| 8,518,667 | B2 * | 8/2013 | Wang | C07K 16/46 435/69.1 |
| 11,267,863 | B2 * | 3/2022 | Kim | C07K 14/635 |

FOREIGN PATENT DOCUMENTS

| | | | |
|---|---|---|---|
| CN | 1167155 | | 12/1997 |
| CN | 101172996 | | 5/2008 |
| CN | 101172996 | A * | 5/2008 |
| CN | 110305223 | | 10/2019 |
| WO | 9535384 | | 12/1995 |
| WO | 2016089782 | A1 | 6/2016 |
| WO | 2018172921 | | 9/2018 |

OTHER PUBLICATIONS

Kjeldsen T, Brandt J, Andersen AS, Egel-Mitani M, Hach M, Pettersson AF, Vad K. A removable spacer peptide in an Î±-factor-leader/insulin precursor fusion protein improves processing and concomitant yield of the insulin precursor in *Saccharomyces cerevisiae*. Gene. Apr. 17, 1996;170(1):107-12. (Year: 1996).*

EPO, Extended European Search Report for EP Application No. 20831844.4, Jun. 13, 2023.

Hou et al., "Oral administration of a fusion protein containing eight GLP-1 analogues produced in *Escherichia coli* BL21(DE3) in streptozotocin-induced diabetic rats," Biotechnology Letters, 2007, vol. 29.

Hou et al., "High-Level Expression of Fusion Protein Containing 10 Tandem Repeated GLP-1 Analogs in Yeast *Pichia pastoris* and its Biological Activity in a Diabetic Rat Model," Bioscience, Biotechnology, and Biochemistry, 2007, vol. 71, No. 6.

Chen et al., "Fusion Protein Linkers: Property, Design and Functionality," Advanced Drug Delivery Reviews, 2013, vol. 65, No. 10.

Zhang et al., "Coordinate expression of multiple proteins in plant cells by exploiting endogenous kex2p-like protease activity," Plant Biotechnology Journal, 2011, vol. 9.

WIPO, International Search Report for International Application No. PCT/CN2020/097058, Sep. 23, 2020.

CNIPA, First Office Action for CN Application No. 201910563692.3, Mar. 1, 2021.

EPO, Communication for EP Application No. 20831844.4, Jul. 4, 2025.

* cited by examiner

*Primary Examiner* — Sharmila G Landau
*Assistant Examiner* — Emily F Eix
(74) *Attorney, Agent, or Firm* — Hodgson Russ LLP

(57) ABSTRACT

Provided in the present disclosure is a fused protein. The fused protein comprises a plurality of target protein sequences, which are connected in series, wherein every two adjacent target protein sequences are connected by means of a linker sequence, the linker sequence is suitable for being cut into a plurality of free target proteins by means of protease, the multiple target protein sequences are not cleaved by the protease, and neither the C-terminus nor the N-terminus of the free target proteins contains additional residues.

18 Claims, 19 Drawing Sheets

Specification includes a Sequence Listing.

M: Middle range protein Marker

| Supernatant of crushed bacteria expressing EEAEAEARG | Precipitate of crushed bacteria expressing EEAEAEARG | Supernatant of crushed bacteria not expressing EEAEAEARG | Precipitate of crushed bacteria not expressing EEAEAEARG |
|---|---|---|---|

| Digestion in the absence of EEAEAEARG | Digestion in the presence of EEAEAEARG |
|---|---|

METHOD FOR PREPARING TARGET POLYPEPTIDE BY MEANS OF RECOMBINATION AND SERIES CONNECTION OF FUSED PROTEINS

CROSS-REFERENCE TO RELATED APPLICATIONS

This application is a continuation of International Application No. PCT/CN2020/097058 filed on Jun. 19, 2020, which claims priority to Chinese Patent Application No. 201910563692.3 filed on Jun. 26, 2019, the entire contents of which are incorporated herein by reference.

FIELD

The present disclosure relates to the field of biomedicine, in particular to a fusion protein, a method and system for obtaining a fusion protein, more particularly to a fusion protein, a method and system for obtaining a fusion protein, a nucleic acid, a construct and a recombinant cell.

BACKGROUND

Polypeptide often refers to an active compound composed of 100 amino acids or below. A polypeptide drug refers to a polypeptide or its modifications for the prevention, diagnosis or treatment of diseases. The polypeptide drugs have been widely applied in many disease fields. For example, the FDA has approved about 70 polypeptide drugs. The polypeptide drugs exhibit significant efficacy on diseases such as diabetes, osteoporosis, intestinal diseases, thrombocytopenia, tumors, cardiovascular diseases, antiviral, immune diseases or the like.

Preproglucagon is a precursor polypeptide consisting of 158 amino acids, which is differentially processed in tissues to form a variety of structurally related glucagon-like peptides, including glucagon, glucagon-like peptide-1 (GLP-1), glucagon-like peptide-2 (GLP-2) or the like. These molecules are involved in a variety of physiological functions, including glucose homeostasis, insulin secretion, gastric emptying and intestinal growth, and regulation of food intake.

Glucagon-like peptides and analogs are mainly prepared by the methods of natural extraction, artificial chemical synthesis and genetic engineering. At present, polypeptide drugs are mainly synthesized by artificial chemical synthesis. However, the cost of solid-phase synthesis is relatively high; a large amount of organic solvents used may have an impact on the activity of peptides; and it is difficult to analyze related substances of solid-phase synthesized peptides, and related substances such as broken peptides, epimers, chiral isomers and the like need to be strictly controlled. The published patent (CN201210369966) discloses an artificial chemical synthesis method for preparing Liraglutide.

At present, there is a need for biomedical researchers to seek solutions for efficiently obtaining polypeptide drugs which not only meet the medical standards but also have minimized toxic and side effects by use of genetic engineering methods.

SUMMARY

The present disclosure aims to at least solve one of technical problems existing in the related art to a certain extent.

A first aspect of embodiments of the present disclosure proposes a fusion protein. According to embodiments of the present disclosure, the fusion protein includes a plurality of target protein sequences connected in series, wherein every two adjacent target protein sequences are connected by a linker sequence, the linker sequence is capable of being cleaved by a protease to form the plurality of the target protein sequences in a free form, the plurality of the target protein sequences each are not cleaved by the protease, and neither a C-terminus nor an N-terminus of the target protein sequence in the free form contains additional residues. It should be noted that "the plurality of the target protein sequences each are not cleaved by the protease" in the present disclosure means that the target protein sequences cannot be cleaved internally by the protease. That is, the protease cannot cleave the internal peptide bond of the target protein sequence. In some embodiments, the expression "not cleaved by the protease" includes "substantially not cleaved by the protease".

The "additional residues" in the present disclosure refer to amino acid residues other than the target protein sequence. The fusion protein according to the embodiments of the present disclosure can be cleaved to the plurality of the target protein sequences in the free form under the action of protease. Neither the C-terminus nor the N-terminus of the target protein sequence in the free form contains additional residues. Therefore, the quality of the target protein sequence is significantly improved, which greatly facilitates the purification of subsequent products. Further, the safety of the target protein sequence as a pharmaceutical polypeptide is significantly increased and the immunotoxicity thereof is significantly reduced.

According to embodiments of the present disclosure, the fusion protein may further include at least one of the following additional technical features.

According to embodiments of the present disclosure, at least a part of the linker sequence constitutes a part of the C-terminus of a protease cleavage product.

According to embodiments of the present disclosure, the linker sequence is consisted of at least one protease recognition site.

According to embodiments of the present disclosure, the linker sequence constitutes the C-terminus of a protease cleavage product. Particularly, the C-terminus of the protease cleavage product is consecutive lysine-arginine (KR) and the protease is Kex2 protease. Further, the consecutive KR at the C-terminus of the protease cleavage product is recognized by the Kex2 and the peptide bond after the arginine (R) (i.e., carboxyl terminal R) is cleaved by the Kex2 to form the plurality of the target protein sequences in the free form.

According to embodiments of the present disclosure, the linker sequence comprises a first protease recognition site and a second protease recognition site, and the plurality of the target protein sequences each do not comprise the second protease recognition site. The first protease recognition site is recognized and cleaved by a first protease to form a first protease cleavage product and the N-terminus of the first protease cleavage product does not carry any residue of the linker sequence. The second protease recognition site is recognized and cleaved by a second protease and the second protease is capable of cleaving the C-terminus of the first protease cleavage product to form the plurality of the target proteins sequences in the free form. Neither the C-terminus nor the N-terminus of the target protein sequence in the free form contains a residue of the linker sequence.

According to embodiments of the present disclosure, the plurality of the target protein sequences comprise at least one first internal protease recognition site and the first internal protease recognition site is recognized by the first protease. The recognition efficiency to the first internal protease recognition site by the first protease is lower than the recognition efficiency to the first protease recognition site in the linker sequence by the first protease. Therefore, the first protease recognition site in the linker sequence is cleaved by the first protease, while the first internal protease recognition site in the target protein sequence is not cleaved by the first protease under a certain condition. In some embodiments, the expression "not cleaved by the first protease" includes "substantially not cleaved by the first protease".

According to embodiments of the present disclosure, the first protease is Kex2 protease. The first internal protease recognition site is at least one of lysine-lysine (KK) and arginine-lysine (RK). The first protease recognition site in the linker sequence is lysine-arginine (KR), arginine-arginine (RR) or arginine-lysine-arginine (RKR). Present inventors have found that the protease Kex2 is capable of recognizing KR or RR, or KK or RK, in which the cleavage ability of Kex2 on KR or RR is significantly stronger than that on KK or RK. It is also discovered by the present inventors that by adapting the amount of Kex2, the KR, RR or RKR in the linker sequence can be specifically recognized and cleaved by the Kex2, while the peptide bond after the K (i.e., carboxyl terminal K) of KK or RK in the linker sequence is not cleaved by the Kex2. In an illustrative example, the enzyme cleavage means as described above can be realized when the mass ratio of the fusion protein to the Kex2 is 2000:1.

According to embodiments of the present disclosure, a sequence before or after the first internal protease recognition site comprises a consecutive acidic amino acid sequence adjacent to the first internal protease recognition site. The present inventors have discovered that the adjacent consecutive acidic amino acid sequence is capable of hiding the first internal protease recognition site in the target protein sequence, such that the first internal protease recognition site in the target protein sequence cannot be recognized and cleaved by the first protease.

According to embodiments of the present disclosure, the consecutive acidic amino acid sequence is of a length of 1 to 2 amino acids. The present inventors have discovered that the consecutive acidic amino acid sequence with the length of 1 to 2 amino acids is capable of effectively hiding the first internal protease recognition site in the target protein sequence.

According to embodiments of the present disclosure, the acidic amino acid is aspartic acid or glutamic acid, preferably the acidic amino acid is aspartic acid. The present inventors have discovered that when the adjacent consecutive acidic amino acid sequence is aspartic acid, the first internal protease recognition site in the target protein sequence is hidden more significantly.

According to embodiments of the present disclosure, the first protease recognition site and the second protease recognition site have an overlapping domain.

According to embodiments of the present disclosure, the first protease recognition site and the second protease recognition site are same or different.

According to embodiments of the present disclosure, the first protease recognition site and the second protease recognition site meet one of the following conditions:

the amino acid sequence of the target protein sequence does not have consecutive lysine-arginine (KR) or arginine-arginine (RR) and optionally does not have consecutive lysine-lysine (KK) or arginine-lysine (RK), the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease;

the amino acid sequence of the target protein sequence does not have lysine (K) and has arginine (R), the first protease recognition site is lysine (K) and the first protease is Lys-C protease, and the second protease recognition site is carboxyl terminal lysine (K) and the second protease is CPB protease;

the amino acid sequence of the target protein sequence does not have both lysine (K) and arginine (R), the first protease recognition site is lysine (K) or arginine (R) and the first protease is Lys-C or Trp protease, and the second protease recognition site is carboxyl terminal lysine (K) or arginine (R) and the second protease is CPB protease; and the amino acid sequence of the target protein sequence has consecutive lysine-arginine (KR), arginine-arginine (RR), lysine-lysine (KK) or arginine-lysine (RK) and the consecutive lysine-arginine (KR), arginine-arginine (RR), lysine-lysine (KK) or arginine-lysine (RK) is adjacent to 1 or 2 consecutive acidic amino acids, the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease.

According to the first protease recognition site and the second protease recognition site under the above conditions in embodiments of the present disclosure, the fusion protein is specifically cleaved at the first protease recognition site to obtain a first protease cleavage product, in which the N-terminus of the first protease cleavage product does not carry any residue of the linker sequence. The first protease cleavage product is further cleaved by a second protease by sequentially cleaving the residue of the linker sequence at the C-terminus of the first protease cleavage product.

According to embodiments of the present disclosure, the fusion protein comprises a plurality of linker sequences. The plurality of the linker sequences are same or different.

According to embodiments of the present disclosure, the linker sequence has a length of 1 to 10 amino acids. According to an illustrative embodiment of the present disclosure, the linker sequence may include 1 to 5 of the first protease recognition site and 1 to 5 of the second protease recognition site. Therefore, the effectiveness of the protease cleavage is ensured.

According to embodiments of the present disclosure, the fusion protein further comprises an auxiliary peptide segment. A carboxyl terminus of the auxiliary peptide segment is connected to the N-terminus of the plurality of the target protein sequences connected in series via the linker sequence. The auxiliary peptide segment can be cleaved from the fusion protein under the action of the protease. The N-terminus of the target protein sequence after cleavage does not contain any residue of the linker sequence.

According to embodiments of the present disclosure, the auxiliary peptide segment comprises a tag sequence and optionally an expression promoting sequence. The linker sequence is capable of facilitating subsequent identification or purification of the fusion protein, and the expression promoting sequence greatly improves the expression efficiency of the fusion protein.

According to embodiments of the present disclosure, the amino acid sequence of the tag sequence is a repeated histidine (His) sequence.

According to embodiments of the present disclosure, the amino acid sequence of the expression promoting sequence is EEAEAEA (SEQ ID NO: 19), EEAEAEAGG (SEQ ID NO: 20) or EEAEAEARG (SEQ ID NO: 21).

The present inventors have found that when the expression promoting sequence has the amino acid sequence as shown above, the expression level and expression efficiency of the fusion protein are greatly improved.

According to embodiments of the present disclosure, the first amino acid of the auxiliary peptide segment is methionine (Met). According to embodiments of the present disclosure, the methionine can be cleaved in the subsequent enzymatic cleavage process along with the excision of the auxiliary peptide segment, thereby avoiding the defects of not completely cleaved methionine, non-uniformity at N-terminus and immunotoxicity regarding the target protein.

According to embodiments of the present disclosure, the target protein sequence is of a length of 10 to 100 amino acids.

According to embodiments of the present disclosure, the fusion protein comprises 4 to 16 target protein sequences connected in series. The present inventors have found that when the fusion protein comprises 4 to 16 target protein sequences connected in series, it is ensured that the loss rate of plasmid within 80 generations is not higher than 10% and thus the expression level of target proteins is basically not affected, thereby being capable of realizing the industrial scale fermentation, obtaining high density and high expression level of target proteins.

According to embodiments of the present disclosure, the target protein sequence is of an amino acid sequence as shown in SEQ ID NOs: 1 to 6.

(SEQ ID NO: 1)
His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile-Ala-
Trp-Leu-Val-Arg-Gly-Arg-Gly (SEQ ID NO: 2)
Glu-Gly-Thr-Phe-Thr-Ser-Asp-Val-Ser-Ser-Tyr-Leu-
Glu-Gly-Gln-Ala-Ala-Lys-Glu-Phe-Ile-Ala-Trp-Leu-
Val-Arg-Gly-Arg-Gly (SEQ ID NO: 3)
Thr-Phe-Thr-Ser-Asp-Val-Ser-Ser-Tyr-Leu-Glu-Gly-
Gln-Ala-Ala-Lys-Glu-Phe-Ile-Ala-Trp-Leu-Val-Arg-
Gly-Arg-Gly (SEQ ID NO: 4)
His-Gly-Asp-Gly-Ser-Phe-Ser-Asp-Glu-Met-Asn-Thr-
Ile-Leu-Asp-Asn-Leu-Ala-Ala-Arg-Asp-Phe-Ile-Asn-
Trp-Leu-Ile-Gln-Thr-Lys-Ile-Thr-Asp (SEQ ID NO: 5)
His-Ser-Gln-Gly-Thr-Phe-Thr-Ser-Asp-Tyr-Ser-Lys-
Tyr-Leu-Asp-Ser-Arg-Arg-Ala-Gln-Asp-Phe-Val-Gln-
Trp-Leu-Met-Asn-Thr

-continued (SEQ ID NO: 6)
Ser-Asp-Lys-Pro-Asp-Met-Ala-Glu-Ile-Glu-Lys-Phe-
Asp-Lys-Ser-Lys-Leu-Lys-Lys-Thr-Glu-Thr-Gln-Glu-
Lys-Asn-Pro-Leu-Pro-Ser-Lys-Glu-Thr-Ile-Glu-Gln-
Glu-Lys-Gln-Ala-Gly-Glu-Ser A second aspect of embodiments of the present disclosure proposes a method for obtaining a target protein sequence in a free form. According to embodiments of the present disclosure, the method includes:

providing a fusion protein as described in the above aspect, contacting the fusion protein with a protease to obtain a plurality of the target protein sequences in the free form, wherein:

the protease is determined based on a linker sequence, the plurality of the target protein sequences each are not cleaved by the protease, and neither a C-terminus nor an N-terminus of the target protein sequence in the free form contains additional residues.

The target protein sequence in the free form obtained via the method according to the embodiments of the present disclosure does not contain additional residues at the C-terminus and the N-terminus. Therefore, the quality of the target protein sequence is significantly improved, which greatly facilitates the purification of subsequent products. Further, the safety of the target protein sequence as a pharmaceutical polypeptide is significantly increased and the immunotoxicity thereof is significantly reduced.

According to embodiments of the present disclosure, the method may further include at least one of the following additional technical features.

According to embodiments of the present disclosure, the linker sequence constitutes the C-terminus of a protease cleavage product. The C-terminus of the protease cleavage product is consecutive lysine-arginine (KR), and the protease is Kex2 protease. Further, the consecutive KR at the C-terminus of the protease cleavage product is recognized by the Kex2 and the peptide bond after the arginine (R) (i.e., carboxyl terminal R) is cleaved by the Kex2 to form the plurality of the target protein sequences in the free form.

According to embodiments of the present disclosure, the linker sequence comprises a first protease recognition site and a second protease recognition site, and the plurality of the target protein sequences each do not comprise the second protease recognition site. The step of contacting the fusion protein with a protease further comprises:

contacting the fusion protein with a first protease to obtain a first protease cleavage product, wherein the N-terminus of the first protease cleavage product does not carry any residue of the linker sequence, contacting the first protease cleavage product with a second protease to obtain the plurality of the target protein sequences in the free form, wherein the second protease is capable of cleaving the C-terminus of the first protease cleavage product.

According to embodiments of the present disclosure, the plurality of the target protein sequences comprise at least one first internal protease recognition site and the first internal protease recognition site is recognized by the first protease. The recognition efficiency to the first internal protease recognition site by the first protease is lower than the recognition efficiency to the first protease recognition site in the linker sequence by the first protease. Therefore, the first protease recognition site in the linker sequence is cleaved by the first protease, while the first internal protease recognition site in the target protein sequence is not cleaved by the first protease under a certain condition.

According to embodiments of the present disclosure, the first internal protease recognition site is at least one of lysine-lysine (KK) and arginine-lysine (RK). The first protease recognition site in the linker sequence is lysine-arginine (KR), arginine-arginine (RR) or arginine-lysine-arginine (RKR) and the second protease recognition site is carboxyl terminal arginine (R) or lysine (K). The first protease is Kex2 protease and the second protease is CPB protease. The mass ratio of the fusion protein to the first protease is 2000:1. The present inventors have found that the protease Kex2 is capable of recognizing KR or RR, or KK or RK, in which the cleavage ability of Kex2 on KR or RR is significantly stronger than that on KK or RK. It is also discovered by the present inventors that by adapting the amount of Kex2, the KR, RR or RKR in the linker sequence can be specifically recognized and cleaved by Kex2, while the peptide bond after the K (i.e., carboxyl terminal K) of KK or RK in the linker sequence is not cleaved by the Kex2. In an illustrative example, the enzyme cleavage means as described above can be realized when the mass ratio of the fusion protein to the Kex2 is 2000:1.

According to embodiments of the present disclosure, a sequence before or after the first internal protease recognition site comprises a consecutive acidic amino acid sequence adjacent to the first internal protease recognition site. The present inventors have discovered that the adjacent consecutive acidic amino acid sequence is capable of hiding the first internal protease recognition site in the target protein sequence, such that the first internal protease recognition site in the target protein sequence cannot be recognized and cleaved by the first protease.

According to embodiments of the present disclosure, the consecutive acidic amino acid sequence is of a length of 1 to 2 amino acids. The present inventors have discovered that the consecutive acidic amino acid sequence with the length of 1 to 2 amino acids is capable of effectively hiding the first internal protease recognition site in the target protein sequence.

According to embodiments of the present disclosure, the acidic amino acid is aspartic acid or glutamic acid, preferably the acidic amino acid is aspartic acid. The present inventors have discovered that when the adjacent consecutive acidic amino acid sequence is aspartic acid, the first internal protease recognition site in the target protein sequence is hidden more significantly.

According to illustrative embodiments of the present disclosure, the plurality of the target protein sequences comprise consecutive aspartic acid-lysine-arginine (DKR), aspartic acid-arginine-arginine (DRR), aspartic acid-lysine-lysine (DKK) or aspartic acid-arginine-lysine (DRK), the first protease recognition site is lysine-arginine (KR), arginine-arginine (RR) or arginine-lysine-arginine (RKR) and the second protease recognition site is the carboxyl terminal arginine (R) or lysine (K), and the first protease is Kex2 protease and the second protease is CPB protease. Thus, only the first protease recognition site in the linker sequence can be recognized and cleaved by the first protease Kex2, while the consecutive DKR, DRR, DKK or DRK in the target protein sequence cannot be recognized and cleaved by the first protease Kex2. The first protease cleavage product is further cleaved by a second protease by sequentially cleaving the residue of the linker sequence at the C-terminus of the first protease cleavage product.

According to embodiments of the present disclosure, the plurality of the target protein sequences do not comprise both the first protease recognition site and the second protease recognition site.

According to embodiments of the present disclosure, the first protease and the second protease both meet one of the followings:

- the amino acid sequence of the target protein sequence does not have consecutive lysine-arginine (KR), arginine-arginine (RR), lysine-lysine (KK) or arginine-lysine (RK), the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease;
- the amino acid sequence of the target protein sequence does not have lysine (K) and has arginine (R), the first protease recognition site is lysine (K) and the first protease is Lys-C, and the second protease recognition site is carboxyl terminal lysine (K) and the second protease is CPB protease; and
- the amino acid sequence of the target protein sequence does not have both lysine (K) and arginine (R), the first protease recognition site is lysine (K) or arginine (R) and the first protease is Lys-C or Trp protease, and the second protease recognition site is carboxyl terminal lysine (K) or arginine (R) and the second protease is CPB protease.

According to the first protease recognition site and the second protease recognition site under the above conditions in embodiments of the present disclosure, the fusion protein is specifically cleaved at the first protease recognition site in the linker sequence to obtain a first protease cleavage product, in which the N-terminus of the first protease cleavage product does not carry any residue of the linker sequence. The first protease cleavage product is further cleaved by a second protease by sequentially cleaving the residue of the linker sequence at the C-terminus of the first protease cleavage product.

According to embodiments of the present disclosure, the mass ratio of the fusion protein to the first protease is 250:1 to 2000:1. The present inventors have found that when the mass ratio of the fusion protein to the first protease is within the range as described above, the fusion protein can be cleaved effectively, with a high cleavage specificity and complete cleavage effect, and producing few non-specific cleavage products.

According to embodiments of the present disclosure, the fusion protein is obtained by fermentation of a microorganism carrying a nucleic acid encoding the fusion protein. Therefore, the defects of high cost caused by artificially synthesized peptides and deterioration of peptide activity by organic solvents can be overcome.

According to embodiments of the present disclosure, the microorganism is *Escherichia coli*. The present inventors observed that when a recombinant yeast system is used to express a heterologous protein, the heterologous protein may be degraded by a plurality of protease families contained in the yeast system, especially small peptides with simple structures which can be easily degraded. The fusion protein to be obtained in this disclosure has a simple structure rather a complex high-level structure and does not have glycosylation sites, thus it is more suitable to use the

*Escherichia coli* to express the present fusion protein. Since *Escherichia coli* just contains a few of proteases, its recombinant expression system is capable of generating active intermediate products in complete structures. The fermentation period of *Escherichia coli* is short, and thus the production cost is greatly reduced.

According to embodiments of the present disclosure, the method further comprises subjecting the fermentation product of the microorganism to crushing and dissolving. The dissolving is performed in the presence of a detergent to obtain the fusion protein. The detergent is a surfactant, which is useful in increasing the solubility of the fusion protein and improving the protease cleavage efficiency.

The selection of detergents in this disclosure is not particularly limited. The kinds of detergents or combinations of detergents can be selected according to the nature of the protease used. According to illustrative embodiments of the present disclosure, the surfactant as the detergent includes: (a) nonionic surfactants such as PEG2000, Tween, sorbitol, urea, TritonX-100, guanidine hydrochloride; (b) anionic surfactants such as sodium lauryl sulfate, sodium lauryl sulfonate, stearic acid; (c) amphoteric surfactants such as tri-sulfopropyltetradecyl dimethyl betaine, Dodecyl dimethyl betaine, lecithin; (d) cationic surfactants such as quaternary ammonium compounds or the like. The detergent is capable of facilitating the dissolution of the fusion protein in a high-efficiency manner and would not deteriorate the activity of the target protein, thus the detergent will not affect the activities of subsequent first protease and second protease.

A third aspect of embodiments of the present disclosure proposes a nucleic acid. According to embodiments of the present disclosure, the nucleic acid encodes a fusion protein as described in the above aspects.

According to embodiments of the present disclosure, the nucleic acid may further include at least one of the following additional technical features.

According to embodiments of the present disclosure, the nucleic acid is of a nucleotide sequence as shown in any one of SEQ ID NOs: 7 to 12.

(SEQ ID NO: 7)

```
CAT ATG CAT CAC CAT CAC GAA GAG GCG GAA GCC GAG GCC CGT GGT AAA

CGT CAC GCA GAG GGC ACC TTT ACG TCT GAT GTT AGC TCT TAT CTG GAA GGT

CAA GCG GCT AAA GAG TTC ATT GCT TGG TTA GTG CGC GGT CGT GGT AAA CGT

CAT GCT GAG GGC ACG TTT ACT AGT GAT GTG TCT AGC TAC CTG GAA GGC CAG

GCC GCA AAA GAG TTC ATC GCG TGG CTG GTT CGC GGT CGT GGT AAA CGT CAT

GCT GAA GGT ACG TTT ACC AGC GAT GTT AGC TCT TAT TTA GAG GGT CAG GCT

GCG AAA GAA TTC ATC GCT TGG TTA GTT CGC GGT CGT GGC AAA CGT CAT GCT

GAG GGC ACC TTT ACG AGC GAC GTG AGT AGC TAC CTG GAA GGC CAG GCC

GCA AAA GAG TTC ATC GCG TGG CTG GTG CGT GGC CGC GGT TAA TGA GGA TCC
```

(SEQ ID NO: 8)

```
CAT ATG CAC CAT CAT CAT GAG GAA GCG GAG GCG GAA GCG CGT GGC AAG

CGT GAG GGC ACC TTC ACC AGC GAC GTG AGC AGC TAC CTG GAG GGT CAG GCG

GCG AAG GAA TTC ATC GCG TGG CTG GTG CGT GGT CGT GGC AAA CGT GAA GGT

ACC TTT ACC AGC GAT GTT AGC AGC TAT CTG GAG GGC CAA GCG GCG AAG GAA

TTC ATT GCG TGG CTG GTT CGC GGT CGT GGC AAA CGT GAG GGT ACC TTT ACC

AGC GAC GTT AGC AGC TAC CTG GAA GGC CAG GCG GCG AAA GAG TTT ATT GCG

TGG CTG GTT CGT GGC CGC GGT AAG CGC GAA GGC ACC TTT ACC AGC GAT GTG

AGC AGC TAT CTG GAA GGT CAA GCG GCG AAA GAA TTT ATC GCG TGG CTG GTG

CGC GGT CGT GGC TAA TGA GGA TCC
```

(SEQ ID NO: 9)

```
CAT ATG CAT CAC CAT CAC GAA GAG GCG GAA GCC GAG GCC CGT GGT AAA

CGT ACC TTT ACG TCT GAT GTT AGC TCT TAT CTG GAA GGT CAA GCG GCT AAA

GAG TTC ATT GCT TGG TTA GTG CGC GGT CGT GGT AAA CGT ACG TTT ACT AGT

GAT GTG TCT AGC TAC CTG GAA GGC CAG GCC GCA AAA GAG TTC ATC GCG TGG

CTG GTT CGC GGT CGT GGT AAA CGT ACG TTT ACC AGC GAT GTT AGC TCT TAT

TTA GAG GGT CAG GCT GCG AAA GAA TTC ATC GCT TGG TTA GTT CGC GGT CGT

GGC AAA CGT ACC TTT ACG AGC GAC GTG AGT AGC TAC CTG GAA GGC CAG GCC

GCA AAA GAG TTC ATC GCG TGG CTG GTG CGT GGC CGC GGT TAA TGA GGA

TCC
```

-continued (SEQ ID NO: 10)
CAT ATG CAT CAC CAT CAC GAA GAG GCG GAA GCC GAG GCC CGT GGT AAA
CGT CAC GGT GAT GGC TCT TTT AGC GAC GAG ATG AAT ACG ATT CTG GAT AAC
TTA GCG GCT CGT GAC TTC ATC AAT TGG CTG ATT CAA ACC AAA ATC ACG GAT
CGT AAA CGT CAT GGC GAC GGT AGC TTC TCT GAT GAA ATG AAT ACG ATT CTG
GAT AAC TTA GCG GCT CGT GAC TTC ATC AAT TGG CTG ATT CAA ACC AAA ATC
ACG GAT CGT AAA CGT CAT GGC GAC GGT AGC TTC TCT GAT GAA ATG AAT ACG
ATT CTG GAT AAC TTA GCG GCT CGT GAC TTC ATC AAT TGG CTG ATT CAA ACC
AAA ATC ACG GAT CGT AAA CGT CAT GGC GAC GGT AGC TTC TCT GAT GAA ATG
AAT ACG ATT CTG GAT AAC TTA GCG GCT CGT GAC TTC ATC AAT TGG CTG ATT
CAA ACC AAA ATC ACG GAT TAA TGA GGA TCC (SEQ ID NO: 11)
CAT ATG CAT CAC CAT CAC GAA GAG GCG GAA GCC GAG GCC CGT GGT AAA
CGT CAT AGC CAG GGT ACC TTT ACC AGT GAT TAT AGC AAA TAT CTG GAT AGC
CGT CGC GCA CAG GAT TTT GTG CAA TGG CTG ATG AAT ACC CGT AAA CGC CAT
TCA CAG GGT ACC TTT ACC AGC GAT TAC AGC AAA TAT CTG GAT AGC CGT CGC
GCA CAG GAT TTT GTT CAG TGG CTG ATG AAT ACC CGC AAA CGT CAT AGC CAG
GGT ACC TTT ACC AGT GAT TAT AGC AAA TAT CTG GAT TCC CGC CGT GCG CAG
GAT TTC GTT CAG TGG CTG ATG AAT ACC CGC AAA CGT CAT AGC CAG GGT ACC
TTT ACC AGC GAT TAT AGC AAA TAT CTG GAT AGC CGT CGT GCG CAG GAT TTC
GTT CAG TGG CTG ATG AAT ACC CGT AAA CGC CAT AGC CAA GGC ACC TTT ACC
AGC GAT TAC AGC AAA TAC CTG GAT AGC CGT CGC GCA CAG GAT TTT GTT CAG
TGG CTG ATG AAT ACC CGC AAA CGT CAT TCA CAG GGT ACC TTT ACC AGC GAT
TAC AGC AAA TAT CTG GAT AGC CGT CGC GCG CAG GAT TTT GTT CAG TGG CTG
ATG AAT ACC CGC AAA CGT CAT AGC CAG GGT ACC TTT ACC AGC GAT TAT AGC
AAA TAT CTG GAT TCC CGC CGT GCA CAG GAT TTC GTT CAG TGG CTG ATG AAT
ACC CGC AAA CGT CAT AGC CAG GGT ACC TTT ACC AGC GAT TAC AGC AAA TAT
CTG GAT AGC CGT CGT GCG CAG GAT TTC GTT CAG TGG CTG ATG AAT ACC TAA
TGA GGA TCC (SEQ ID NO: 12)
CAT ATG CAC CAT CAT CAT GAG GAA GCG GAG GCG GAA GCG CGT GGC AAG
CGT AGC GAC AAA CCG GAT ATG GCG GAG ATC GAA AAG TTC GAC AAG AGC AAA
CTG AAG AAA ACC GAG ACC CAG GAA AAG AAC CCG CTG CCG AGC AAA GAG ACC
ATC GAG CAG GAA AAG CAA GCG GGC GAA AGC CGT AAA CGT AGC GAT AAG CCG
GAC ATG GCG GAG ATT GAA AAG TTC GAT AAG AGC AAG CTG AAG AAA ACC GAA
ACC CAA GAA AAG AAC CCG CTG CCT AGC AAG GAA ACC ATT GAA CAG GAA AAG
CAA GCG GGT GAA AGC CGT AAG CGT AGC GAT AAA CCG GAC ATG GCG GAA ATT
GAA AAA TTT GAT AAA TCT AAG CTG AAG AAA ACC GAG ACT CAG GAA AAG AAC
CCG CTG CCA AGC AAG GAA ACC ATT GAG CAA GAG AAA CAG GCG GGT GAG AGC
CGT AAA CGT TCT GAT AAG CCG GAT ATG GCG GAA ATC GAG AAA TTT GAC AAA
TCT AAA CTG AAG AAA ACC GAA ACT CAG GAA AAG AAC CCG CTG CCC AGC AAA
GAG ACC ATT GAG CAG GAA AAA CAA GCG GGT GAA AGC TAA TGA GGA TCC A fourth aspect of embodiments of the present disclosure proposes a construct. According to embodiments of the present disclosure, the construct carries a nucleic acid as described in the above aspect. Further, when the construct according to the embodiments of the present disclosure is introduced into a receptor cell, the expression of the aforementioned fusion protein is realized under conditions suitable for protein expression.

A fifth aspect of embodiments of the present disclosure proposes a recombinant cell. According to embodiments of the present disclosure, the recombinant cell comprises a nucleic acid as described in the above aspect, or a construct as described in the above aspect, or express a fusion protein as described in the above aspects.

According to embodiments of the present disclosure, the recombinant cell may further include at least one of the following additional technical features.

According to embodiments of the present disclosure, the recombinant cell is *Escherichia coli* cell.

A sixth aspect of embodiments of the present disclosure proposes a system for obtaining a target protein sequence in a free form. According to embodiments of the present disclosure, the system includes:

a device for providing a fusion protein, configured to provide a fusion protein as described in the above aspects;

a proteolysis device, connected to the device for providing a fusion protein and configured to contact the fusion protein with a protease to obtain a plurality of the target protein sequences in the free form, wherein the protease is determined based on a linker sequence, the plurality of the target protein sequences each are not cleaved by the protease, and neither a C-terminus nor an N-terminus of the target protein sequence in the free form contains additional residues.

The system according to the embodiments of the present disclosure is adaptive to implement the method for obtaining a target protein sequence in a free form described in the above. Neither the C-terminus nor the N-terminus of the target protein sequence in the free form contains additional residues. Therefore, the quality of the target protein sequence is significantly improved, which greatly facilitates the purification of subsequent products. Further, the safety of the target protein sequence as a pharmaceutical polypeptide is significantly increased and the immunotoxicity thereof is significantly reduced.

According to embodiments of the present disclosure, the system may further include at least one of the following additional technical features.

According to embodiments of the present disclosure, the proteolysis device is arranged with a first protease proteolysis unit and a second protease proteolysis unit, and the first protease proteolysis unit is connected to the second protease proteolysis unit. The fusion protein can be cleaved in the first protease proteolysis unit. The first protease cleavage product can be further cleaved in the second protease proteolysis unit. The protease can be artificially added to the first protease proteolysis unit and the second protease proteolysis unit respectively. The first protease and the second protease can be immobilized to realize the cleavage of the fusion protein in an industrialized and automatic manner.

According to embodiments of the present disclosure, the linker sequence constitutes the C-terminus of a protease cleavage product. The C-terminus of the protease cleavage product is consecutive lysine-arginine (KR). The first protease proteolysis unit and the second protease proteolysis unit are immobilized with Kex2 protease. Thus, the target protein sequences in a free form can be obtained after the fusion protein is cleaved in the first protease proteolysis unit. Further, the first protease cleavage product may be cleaved in the second protease proteolysis unit, such that the fusion protein which is not cleaved or is partly cleaved among the first protease cleavage product can be further cleaved to obtain the target protein sequences in a free form. The first protease cleavage product may not be cleaved to obtain the target protein sequences in a free form.

According to embodiments of the present disclosure, the linker sequence comprises a first protease recognition site and a second protease recognition site. The plurality of the target protein sequences each do not comprise the second protease recognition site. The first protease proteolysis unit is immobilized with a first protease and the second protease proteolysis unit is immobilized with a second protease. The fusion protein is contacted with the first protease in the first protease proteolysis unit to obtain a first protease cleavage product, and the N-terminus of the first protease cleavage product does not carry any residue of the linker sequence. The first protease cleavage product is contacted with the second protease in the second protease proteolysis unit to obtain the plurality of the target protein sequences in the free form, wherein the second protease is capable of cleaving the C-terminus of the first protease cleavage product.

According to embodiments of the present disclosure, the amino acid sequence of the target protein sequence does not have consecutive lysine-arginine (KR) or arginine-arginine (RR) and optionally does not have consecutive lysine-lysine (KK) or arginine-lysine (RK), the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease. According to embodiments of the present disclosure, the amino acid sequence of the target protein sequence does not have lysine (K) and has arginine (R), the first protease recognition site is lysine (K) and the first protease is Lys-C protease, and the second protease recognition site is carboxyl terminal lysine (K) and the second protease is CPB protease. According to embodiments of the present disclosure, the amino acid sequence of the target protein sequence does not have both lysine (K) and arginine (R), the first protease recognition site is lysine (K) or arginine (R) and the first protease is Lys-C or Trp protease, and the second protease recognition site is carboxyl terminal lysine (K) or arginine (R) and the second protease is CPB protease. According to embodiments of the present disclosure, the amino acid sequence of the target protein sequence has consecutive lysine-arginine (KR), arginine-arginine (RR), lysine-lysine (KK) or arginine-lysine (RK) and the consecutive lysine-arginine (KR), arginine-arginine (RR), lysine-lysine (KK) or arginine-lysine (RK) is adjacent to 1 or 2 consecutive acidic amino acids, the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease.

According to embodiments of the present disclosure, the device for providing a fusion protein comprises a fermentation unit. The fermentation unit is configured to cause the fermentation of a microorganism carrying a nucleic acid encoding the fusion protein, preferably the microorganism is *Escherichia coli.*

According to embodiments of the present disclosure, the device for providing a fusion protein further comprises a dissolution unit. The dissolution unit is connected to the fermentation unit and is configured to subject the fermentation product of the microorganism to crushing and dissolving, and the dissolving is performed in the presence of a detergent to obtain the fusion protein.

According to embodiments of the present disclosure, the proteolysis device further comprises an adjustment unit. The adjustment unit is configured to adjust the amount of the protease such that the mass ratio of the fusion protein to the protease is 250:1 to 2000:1. Therefore, the specific cleavage of the fusion protein at the protease recognition site of the linker sequence can be realized by adjusting the amount of the protease in the adjustment unit.

The advantages or effects of the additional technical features of the system for obtaining a target protein sequence in a free form as described above in the embodiments of the present disclosure are similar to those of the method for obtaining a target protein sequence in a free form, which is not be repeated.

DETAILED DESCRIPTION OF EMBODIMENTS

Figure 1:
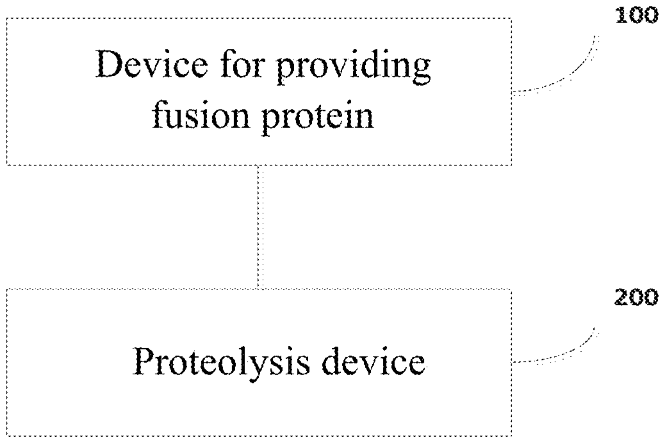
FIG. 1 is a schematic diagram showing the structure of a system for obtaining target protein sequences in a free form according to embodiments of the present disclosure.

Glucagon is mainly useful in treating severe hypoglycemia in diabetic patients who underwent the insulin therapy. The glucagon drug on the market includes GlucaGen. GLP-1 is mainly used for type II diabetes. The GLP-1 receptor agonist drug on the market includes Exenatide, Exenatide QW, Liraglutide, Albiglutide, Dulaglutide, Lixisenatidev and Semaglutide. GLP-2 is mainly used for short bowel syndrome. The GLP-2 drug on the market includes Teduglutide.

Human GLP-1 is a peptide hormone secreted by the intestinal mucosa that promotes the insulin secretion. The GLP-1 regulates blood glucose metabolism by increasing the secretion of insulin and inhibiting the release of glucagon; reduces intestinal peristalsis, causing satiety and thus suppressing appetite; and promotes the proliferation of pancreatic β-cells and inhibits the apoptosis of pancreatic β-cells to increase the number and function of pancreatic β-cells. Importantly, the hypoglycemic effect by GLP-1 merely occurs at a situation of high blood glucose concentration, thereby avoiding hypoglycemia caused by excessively secreted insulin. The GLP-1 can also improve the sensitivity of receptor cells to insulin, which is helpful for the treatment of insulin resistance. GLP-1 long-term treatment can significantly improve the medium and long-term indicators of a patient such as glycosylated hemoglobin. For type II diabetes caused by obesity, GLP-1 can inhibit gastric emptying, help patients to control their diet and achieve weight loss. In the past two years, it has been confirmed that GLP-1 drugs such as Liraglutide and Semaglutide benefit to cardiovascular diseases. Insulin therapy usually has the disadvantages of weight increase and hypoglycemia risk, whereas the GLP-1 receptor agonist drugs just meet these clinical need.

The mechanism of GLP-1 drugs represented by Liraglutide in the treatment of diabetes includes: stimulation of insulin secretion in a physiological and glucose-dependent manner; reduction of glucagon secretion; inhibition of gastric emptying; reduction of appetite; and promotion of growth and recovery of pancreatic β-cells.

When the blood glucose concentration exceeds a normal level, GLP-1 can stimulate the secretion of insulin through the above mechanism so as to decrease the blood glucose concentration. Therefore, GLP-1 is a glucose-dependent hypoglycemic drug which has a high efficacy. GLP-1 is a suitable candidate for the treatment of type 2 diabetes based on its above characteristics and the analysis of its clinical treatment effects for years. Further, the combination of GLP-1 and insulin can exert a better therapeutic effect on a patient in the treatment of type 1 diabetes. GLP-1 can even exert a therapeutic effect on a patient who has failed sulfonylureas therapy and do not cause severe hypoglycemia, thus exhibiting the potency on glucose-lowering. Furthermore, GLP-1 has the ability of increasing the biosynthesis rate of insulin and restoring the rapid response of rat pancreatic β-cells to elevated blood glucose (i.e., prime insulin release). It has been reported in the literature that GLP-1 can stimulate the growth and proliferation of pancreatic β-cells and promote differentiation of ductal cells to new pancreatic β-cells. A number of human trials have shown that GLP-1 is also involved in the preservation and repair of pancreatic β-cell populations.

The competition points of GLP-1 drugs mainly include administration frequency, hypoglycemic effect, weight lowering effect, immunogenicity and the like. The disadvantages of Exenatide mainly lie in a short period of drug elimination and strong immunogenicity. The disadvantages of Albiglutide mainly lie in hypoglycemic effect and weight lowering effect. Although Albiglutide is severed as the first long-acting GLP-1 in an administration frequency of once a week, its efficacy is far inferior to the latter Dulaglutide entering to the market. In addition, the cardiovascular risk raised by GLP-1 drugs has also attracted much attention. For example, Insulin Degludec, which has been marketed in Japan, the European Union and the United States, has been delayed for approval by the US FDA for its cardiovascular risk concerns. Liraglutide and Semaglutide have been proven to have cardiovascular benefits in the past two years, greatly improving the overall market competitiveness of GLP-1 receptor agonist drugs.

With the development of molecular biology technology, more and more peptide drugs on the market are prepared by genetic engineering methods. For example, Liraglutide and Semaglutide are expressed in a recombinant yeast system. When the recombinant yeast system is used to express heterologous proteins, a plurality of protease families contained in the yeast system may degrade the heterologous proteins, especially some small peptides with simple structures which are more easily degraded. The degradation products increase with the extension of fermentation time. The degradation products are hardly separated by purification in an effective means. It is revealed through studies that the degradation in the fermentation process is caused by the digestion of the polypeptide by the protease contained in the yeast. The degradation degree can be partially weakened by replacing the expression host bacteria, adjusting fermentation conditions and the like, but the requirements of industrialization cannot be met. Knockout or inactivation of specific protease genes in host yeast bacteria by molecular biological means can partially prevent the degradation of polypeptides, but it is technically difficult and cannot completely overcome the degradation of polypeptides. For example, Novo Nordisk company utilizes YES2085 *Saccharomyces cerevisiae* (Knock out YPS1 and PEP4 to prevent degradation) to efficiently express $Arg^{34}$-GLP-1 (7-37), referring to US20100317057.

The *Escherichia coli* expression system is also commonly used to express recombinant heterologous proteins. Polypeptide drug has a simple structure rather a complex high-level structure and does not have glycosylation sites. Since *Escherichia coli* just contains a few of proteases, its recombinant expression system is capable of generating active polypeptides in complete structures. By use of conventional *Escherichia coli* recombinant expression system, target polypeptides can be obtained after enzyme digestion. However, the yield and recovery rate of the target polypeptides after enzyme digestion are significantly reduced, which severely restricts the industrialization of polypeptide drugs.

In the published invention patent (CN201610753093.4) associated to the preparation of GLP-1 polypeptides, enterokinase as a chaperone protein is applied for fusion expression of $Arg^{34}$-GLP-1 (7-37). Although the expression level of the fusion protein is relatively high, the $Arg^{34}$-GLP-1 (7-37) after digestion only accounts for one tenth of the total fusion protein, with a low yield of the target protein. In addition, chaperone proteins (TrxA, DsbA) are suitable for the fusion expression of macromolecular proteins that require renaturation. $Arg^{34}$-GLP-1 (7-37) has a simple spatial structure and does not require the renaturation of spatial conformation. In the purification process, it is necessary to strictly control the residual content of the chaperone protein introduced by enzyme digestion in order to prevent the caused safety risks. CN201610857663.4 adopts the recombinant SUMO-GLP-1 (7-37) fusion protein to express GLP-1 (7-37).

In the published invention patents (CN104072604B, CN101171262 or CN102659938A) associated to the preparation of GLP-2 polypeptides, GLP-2 analogues are all prepared by the solid-phase or liquid-phase synthesis methods. The CN103159848A discloses the preparation of a polypeptide of two GLP-2 repeats connected in series. The CN103945861A discloses the preparation of a fusion polypeptide of a recombinant peptide and GLP-2. The CN201610537328.6 of Shanghai Pharmaceutical Industry Research Institute prepares GLP-2 by use of enterokinase and acid cleavage method, in which a strong acid is applied to cleave the linking bond at the acid cleavage site aspartic acid-proline (D-P) in order to obtain a complete GLP-2. During the acid cleavage, broken peptides may be generated due to the damage to the polypeptide. Further, the long-term acid lysis solution may cause deamidation-related substances of the polypeptide, which seriously affects the quality of products and restricts the subsequent purification.

In addition, by use of traditional prokaryotic and eukaryotic cells for recombinant expression, the translation of proteins starts from the first methionine at N-terminus. Therefore, the first amino acid of the expression product is the non-target amino acid methionine. Only when the first amino acid of the target protein has a rotation radius of 1.22 angstroms or less such as Gly and Ala, the N-terminal methionine can be effectively cleaved by the methioninase. However, when the target protein has a high expression level, methionine is usually not cut off due to the saturation of the methioninase for cleaving the methionine and lacking of cofactors. Therefore, non-uniformity at N-terminus (with or without Met) is caused and the amino acid sequence of the expressed protein (with the first position Met) is inconsistent with that of the target protein (without the first position Met), which may cause immunotoxicity.

The embodiments of the present disclosure are described in detail below and examples of the embodiments are shown in the drawings. The embodiments in below are described exemplarily with reference to the drawings. They are intended to explain the present disclosure but should not be construed as limiting the present disclosure.

An aspect of embodiments of the present disclosure provides a fusion protein and a novel method for expressing a recombinant polypeptide in end-to-end series connection to solve the disadvantages of genetically engineered expression of recombinant polypeptides in existing technology.

In the present disclosure, the novel method for expressing a recombinant polypeptide in end-to-end series connection specifically includes the following steps:

a) designing the polypeptide in end-to-end series connection and whole gene synthesizing a DNA sequence encoding the amino acid sequence of the polypeptide, wherein the polypeptide is of a structure of auxiliary peptide segment-(enzyme cleavage site-target protein sequence-enzyme cleavage site-target protein sequence)n, wherein n is 2 to 8;
b) constructing a recombinant plasmid expression vector containing the DNA sequence encoding the amino acid sequence of the polypeptide;
c) transforming the recombinant plasmid expression vector into a host cell to obtain genetically engineered recombinant bacteria expressing the polypeptide;
d) subjecting the genetically engineered recombinant bacteria to fermentation culture in a high density;
e) double digesting the polypeptide via a recombinant alkaline protease to obtain all the target protein sequences; and
f) purifying the target protein sequences by reversed-phase chromatography to obtain high-purity target protein sequences.

According to the present disclosure, the expression vector in step b) refers to an expression vector of *Escherichia coli* containing an expression promoter including T7, Tac, Trp or lac, or a yeast expression vector containing an a secretion factor and an expression promoter AOX or GAP.

The host cell in step c) may be *Pichia pastoris* or *Escherichia coli*, preferably *Escherichia coli*. More specifically, the host cell is *Escherichia coli* BL21, BL21 (DE3) or BL21(DE3) plysS, preferably BL21 (DE3).

The recombinant alkaline protease in step e) is a recombinant double basic amino acid endopeptidase (Recombinant Kex2 Protease, Kex2 for short), a Kex2-like protease on the membrane of a yeast cell. The Kex2 protease specifically hydrolyzes a carboxyl terminal peptide bond in an alpha factor precursor, in particular a carboxyl terminal peptide bond of two consecutive basic amino acids, such as Lys-Arg, Lys-Lys, Arg-Arg or the like. Among them, Lys-Arg has the highest digestion efficiency. The Kex2 protease is of an optimal pH of 9.0 to 9.5. The enzyme digestion buffer for Kex2 protease may be Tris-HCl buffer, phosphate buffer or borate buffer, preferably Tris-HCl buffer. Recombinant carboxypeptidase B (CPB for short) is capable of selectively hydrolyzing arginine (Arg, R) or lysine (Lys, K) at the carboxyl terminus of a protein or polypeptide, preferably hydrolyzing basic amino acids. The CPB protease is of an optimal pH of 8.5 to 9.5. The enzyme digestion buffer for CPB protease may be Tris-HCl buffer, phosphate buffer or borate buffer, preferably Tris-HCl buffer.

The present disclosure has the following advantages compared to the existing technology.

(a) Regarding the novel polypeptide in end-to-end series connection designed, its genetically engineered recombinant bacteria can ensure that the loss rate of plasmid within 80 generations is not higher than 10% and thus the expression level of target proteins is basically not affected, thereby being capable of realizing the industrial scale fermentation, obtaining high density and high expression level of target proteins.
(b) According to the glucagon-like peptides in end-to-end series connection and analogs thereof designed in the present disclosure, all target proteins in complete structures can be obtained after digestion. In contrast, through the conventional method for expressing a fusion protein, although the expression level of fusion protein is relatively high, the undesired proteins are generated and need to be removed after digestion, thus only a part of target proteins corresponding to the molar concentration are obtained.
(c) The design of the present disclosure can completely overcome the non-uniformity defect caused by the methionine (Met) at N-terminus of the fusion protein. Specifically, the N-terminal Met can be completely cleaved via the unique auxiliary peptide segment and the enzyme digestion method in the present disclosure, thus obtaining target proteins having completely uniform N-terminus.
(d) Kex2 protease and recombinant CPB protease have high digestion specificity, ensuring that non-specific digestion related substances are not produced. Therefore, all target proteins with a correct structure can be obtained after digestion, which greatly reduces the difficulty of subsequent purification and separation. Thus, extremely pure target proteins can be obtained, the recovery rate of target proteins is improved and the cost for expression of genetically engineered recombinant polypeptide is reduced.
(e) Reversed-phase chromatography for purification brings a superior separation effect and a high recovery rate.

Another aspect of embodiments of the present disclosure proposes a system for obtaining a plurality of target protein sequences in a free form. According to embodiments of the present disclosure, referring to FIG. 1, the system includes: a device for providing a fusion protein 100, configured to provide the fusion protein as described in the above aspect; a proteolysis device 200, connected to the device for providing a fusion protein 100 and configured to contact the fusion protein with a protease to obtain the plurality of the target protein sequences in a free form, in which the protease is determined based on a linker sequence, the plurality of the target protein sequences each are not cleaved by the protease, and neither a C-terminus nor an N-terminus of the target protein sequence in the free form contains additional residues. The system according to embodiments of the present disclosure is suitable for performing the method for obtaining a plurality of target protein sequences in a free form as described above. Neither the C-terminus nor the N-terminus of the target protein sequence in the free form obtained contains additional residues. The quality of the target proteins is significantly improved and the subsequent purification of target proteins is greatly facilitated. The target protein as a pharmaceutical polypeptide is of significantly improved safety and significantly reduced immunotoxicity.

Figure 2:
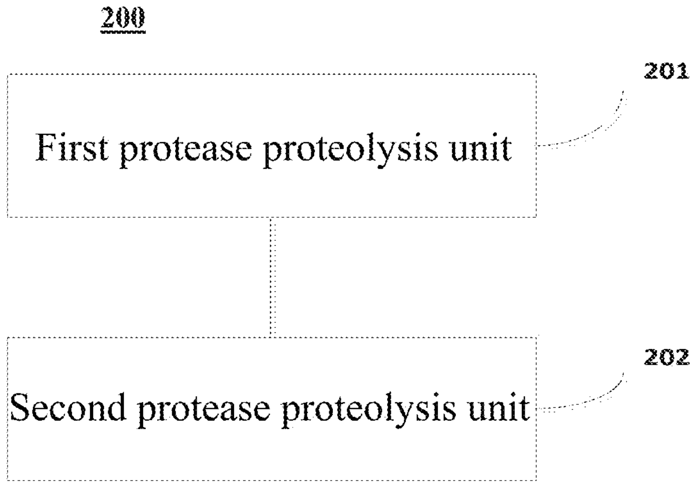
FIG. 2 is a schematic diagram showing the structure of a proteolysis device according to embodiments of the present disclosure.

According to a particular embodiment of the present disclosure, referring to FIG. 2, the proteolysis device is arranged with a first protease proteolysis unit 201 and a second protease proteolysis unit 202, and the first protease proteolysis unit 201 is connected to the second protease proteolysis unit 202. The fusion protein can be cleaved in the first protease proteolysis unit. The first protease cleavage product can be further cleaved in the second protease proteolysis unit. The protease can be artificially added to the first protease proteolysis unit and the second protease proteolysis unit respectively. The first protease and the second protease can be immobilized to realize the cleavage of the fusion protein in an industrialized and automatic manner.

Particularly, in the case that the linker sequence constitutes the C-terminus of a protease cleavage product, the C-terminus of the protease cleavage product is consecutive lysine-arginine (KR), and the first protease proteolysis unit and the second protease proteolysis unit are immobilized with Kex2 protease. Thus, the target protein sequences in a free form can be obtained after the fusion protein is cleaved in the first protease proteolysis unit. Further, the first protease cleavage product may be cleaved in the second protease proteolysis unit, such that the fusion protein which is not cleaved or is partly cleaved among the first protease cleavage product can be further cleaved to obtain the target protein sequences in a free form. The first protease cleavage product may not be cleaved to obtain the target protein sequences in a free form.

Particularly, the linker sequence includes a first protease recognition site and a second protease recognition site, and the plurality of the target protein sequences do not contain the second protease recognition site. The first protease proteolysis unit 201 is immobilized with a first protease and the second protease proteolysis unit 202 is immobilized with a second protease. The fusion protein is contacted with the first protease in the first protease proteolysis unit to obtain a first protease cleavage product, and the N-terminus of the first protease cleavage product does not carry any residue of the linker sequence. The first protease cleavage product is contacted with the second protease in the second protease proteolysis unit to obtain the plurality of the target protein sequences in the free form, in which the second protease is capable of cleaving the C-terminus of the first protease cleavage product.

In the case that the amino acid sequence of the target protein sequence does not have consecutive lysine-arginine (KR) or arginine-arginine (RR) and has or does not have consecutive lysine-lysine (KK) or arginine-lysine (RK), the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease. In the case that the amino acid sequence of the target protein sequence does not have lysine (K) and has arginine (R), the first protease recognition site is lysine (K) and the first protease is Lys-C protease, and the second protease recognition site is carboxyl terminal lysine (K) and the second protease is CPB protease. In the case that the amino acid sequence of the target protein sequence does not have both lysine (K) and arginine (R), the first protease recognition site is lysine (K) or arginine (R) and the first protease is Lys-C or Trp protease, and the second protease recognition site is carboxyl terminal lysine (K) or arginine (R) and the second protease is CPB protease. In the case that the amino acid sequence of the target protein sequence has consecutive lysine-arginine (KR), arginine-arginine (RR), lysine-lysine (KK) or arginine-lysine (RK) and the consecutive lysine-arginine (KR), arginine-arginine (RR), lysine-lysine (KK) or arginine-lysine (RK) is adjacent to 1 or 2 consecutive acidic amino acids, the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease. Therefore, the fusion protein is cleaved in the first protease proteolysis unit, such that the carboxyl-terminal peptide bond at the first protease recognition site of the linker sequence is cleaved to obtain the first protease proteolysis product without any linker sequence residue at the N-terminus. Further, the first protease proteolysis product is cleaved in the second protease proteolysis unit, such that the linker sequence residue at the carboxyl terminus of the first protease proteolysis product is cleaved in sequence to obtain the target protein sequences in a free form without any linker sequence residue at the C-terminus.

According to particular embodiments of the present disclosure, the first protease and the second protease may be simultaneously added in a system to cleave the fusion protein. According to the embodiments of the present disclosure, the first protease and the second protease selected do not affect each other's enzyme activity.

Figure 3:
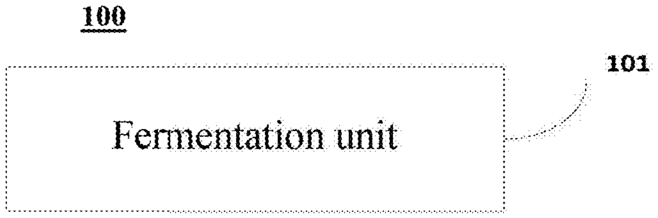
FIG. 3 is a schematic diagram showing the structure of a device for preparing a fusion protein according to embodiments of the present disclosure.

According to embodiments of the present disclosure, referring to FIG. 3, the device for providing a fusion protein includes a fermentation unit 101. The fermentation unit 101 is configured to cause the fermentation of a microorganism carrying a nucleic acid encoding the fusion protein. Preferably, the microorganism is *Escherichia coli.*

Figure 4:
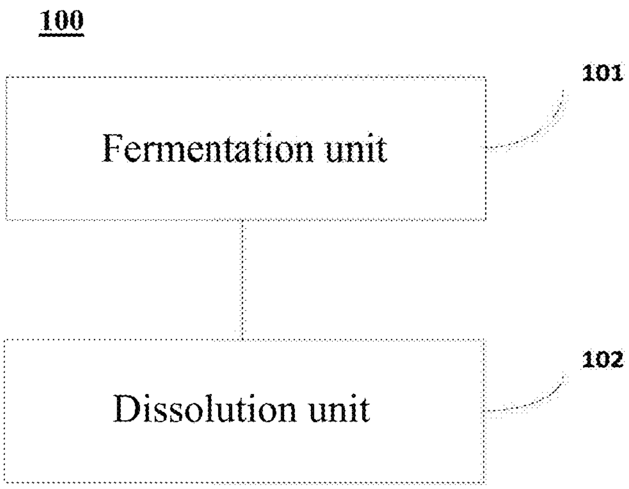
FIG. 4 is another schematic diagram showing the structure of a device for preparing a fusion protein according to embodiments of the present disclosure.

According to embodiments of the present disclosure, referring to FIG. 4, the device for providing a fusion protein further includes a dissolution unit 102. The dissolution unit 102 is connected to the fermentation unit and is configured to subject the fermentation product of the microorganism to crushing and dissolving, and the dissolving is performed in the presence of a detergent to obtain the fusion protein.

Figure 5:
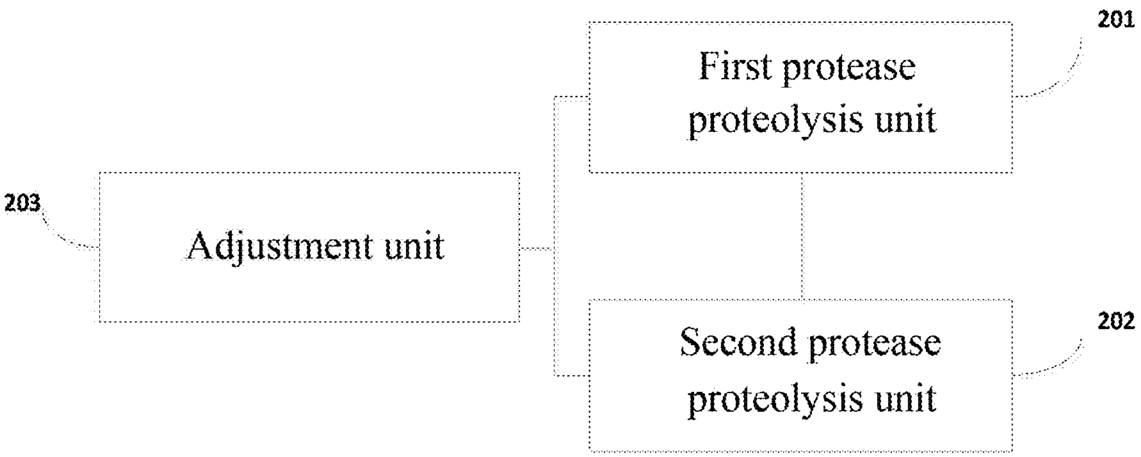
FIG. 5 is another schematic diagram showing the structure of a proteolysis device according to embodiments of the present disclosure.

According to embodiments of the present disclosure, referring to FIG. 5, the proteolysis device further includes an adjustment unit 203. The adjustment unit 203 is configured to adjust the amount of the protease such that the mass ratio of the fusion protein to the protease is 250:1 to 2000:1. The adjustment unit is configured to adjust the amount of the protease, thereby realizing the specific cleavage of the fusion protein at the enzyme cleavage site of the linker sequence.

The present disclosure is further described below in combination with specific embodiments. The advantages and characteristics of the present disclosure will become apparent in the description. These examples are merely illustrative and do not constitute any limitation on the scope of the present disclosure. Those skilled in the art should understand that the details and forms of the technical solutions of the present disclosure can be modified or replaced without departing from the scope of the present disclosure, and these modifications or replacements fall within the scope of the present disclosure.

Example 1 Construction of pET-30a-Arg$^{34}$-GLP-1 (7-37) Recombinant Plasmid and Engineered Recombinant Bacteria According to auxiliary peptide segment-(enzyme cleavage site-target protein sequence-enzyme cleavage site-target protein sequence)$_4$, Arg$^{34}$-GLP-1 (7-37) (SEQ ID NO: 1) repeats were connected in series and formed the sequence shown in SEQ ID NO: 13. The cDNA sequence shown in SEQ ID NO: 7 was designed based on the codon preference of *E. coli* and by adding the Nde I nuclease cleavage site CAT ATG at the 5' end, adding the double stop codons TAA TGA at the 3' end and adding the BamH I nuclease cleavage site GGA TCC. The nucleotide sequence was artificially whole gene synthesized, followed by construction on the PUC-57 vector to obtain a recombinant plasmid PUC-57-Arg$^{34}$-GLP-1 (7-37), which was transformed in *E. coli* bacteria Top10 Glycerol Stock for storage.

```
                                    (SEQ ID NO: 13)
NH2-Met-His-His-His-His-Glu-Glu-Ala-Glu-Ala-Glu-

Ala-Arg-Gly-Lys-Arg-His-Ala-Glu-Gly-Thr-Phe-Thr-

Ser-Asp-Val-Ser-Ser-Tyr-Leu-Glu-Gly-Gln-Ala-Ala-

Lys-Glu-Phe-Ile-Ala-Trp-Leu-Val-Arg-Gly-Arg-Gly-

Lys-Arg-His-Ala-Glu-Gly-Thr-Phe-Thr-Ser-Asp-Val-

Ser-Ser-Tyr-Leu-Glu-Gly-Gln-Ala-Ala-Lys-Glu-Phe-

Ile-Ala-Trp-Leu-Val-Arg-Gly-Arg-Gly-Lys-Arg-His-

Ala-Glu-Gly-Thr-Phe-Thr-Ser-Asp-Val-Ser-Ser-Tyr-

Leu-Glu-Gly-Gln-Ala-Ala-Lys-Glu-Phe-Ile-Ala-Trp-

Leu-Val-Arg-Gly-Arg-Gly-Lys-Arg-His-Ala-Glu-Gly-

Thr-Phe-Thr-Ser-Asp-Val-Ser-Ser-Tyr-Leu-Glu-Gly-

Gln-Ala-Ala-Lys-Glu-Phe-Ile-Ala-Trp-Leu-Val-Arg-

Gly-Arg-Gly-COOH
```

Figure 6:
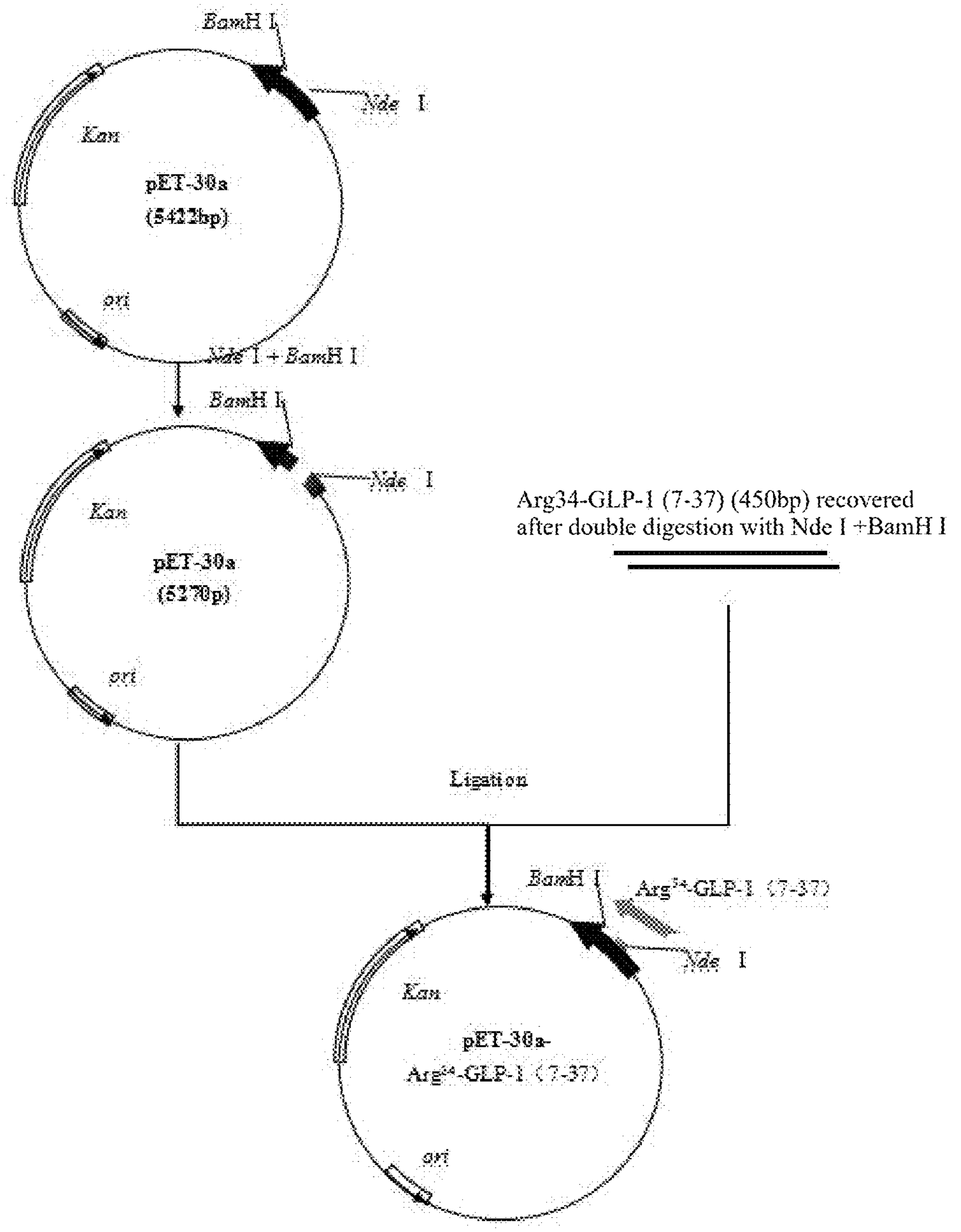
FIG. 6 is a schematic diagram of construction of recombinant plasmid pET-30a-$Arg^{34}$-GLP-1 (7-37) according to embodiments of the present disclosure.
Figure 7:
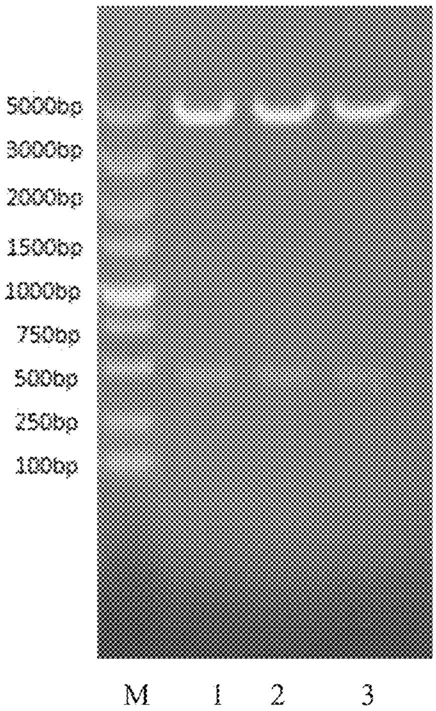
FIG. 7 is a diagram of identification of digestion of pET-30a-$Arg^{34}$-GLP-1 (7-37) according to embodiments of the present disclosure.

The recombinant plasmid PUC-57-Arg$^{34}$-GLP-1 (7-37) was double digested with Nde I/BamH I endonucleases and the target nucleotide sequences were recovered. The target nucleotide sequences were subsequently connected to Nde I/BamH I double-digested plasmid pET-30a (purchased from Novagen) via the T4 DNA ligase. Recombinant plasmids were transformed into the cloning host strain *E. coli* Top10, followed by enzyme digestion and PCR verification to screen the recombinant plasmid pET-30a-Arg$^{34}$-GLP-1 (7-37). After that, the cDNA sequence of Arg$^{34}$-GLP-1 (7-37) in the recombinant plasmid was identified as the correct sequence via the DNA sequencing. The recombinant plasmid pET-30a-Arg$^{34}$-GLP-1 (7-37) was transformed to the expression host strain *Escherichia coli* BL21 (DE3) and engineered recombinant bacteria were obtained via expression screening. A schematic diagram of construction of the recombinant plasmid is shown in FIG. 6. A diagram of identification of digestion of the recombinant plasmid is shown in FIG. 7, in which bands of about 5000 bp and 450 bp both appear after digestion regarding plasmids 1-3, corresponding to pET-30a and Arg$^{34}$-GLP-1 (7-37) respectively and consistent with theoretical values, indicating that Arg$^{34}$-GLP-1 (7-37) is correctly connected to the vector pET-30a.

Example 2 Construction of pET-30a-Arg$^{34}$-GLP-1 (9-37) Recombinant Plasmid and Engineered Recombinant Bacteria According to auxiliary peptide segment-(enzyme cleavage site-target protein sequence-enzyme cleavage site-target protein sequence)$_4$, Arg$^{34}$-GLP-1 (9-37) (SEQ ID NO: 2) repeats were connected in series and formed the sequence shown in SEQ ID NO: 14. The cDNA sequence shown in SEQ ID NO: 8 was designed based on the codon preference of *E. coli* and by adding the Nde I nuclease cleavage site CAT ATG at the 5' end, adding the double stop codons TAA TGA at the 3' end and adding the BamH I nuclease cleavage site GGA TCC. The nucleotide sequence was artificially whole gene synthesized, followed by construction on the PUC-57 vector to obtain a recombinant plasmid PUC-57-Arg$^{34}$-GLP-1 (9-37), which was transformed in *E. coli* bacteria Top10 Glycerol Stock for storage.

```
                                    (SEQ ID NO: 14)
NH2-Met-His-His-His-His-Glu-Glu-Ala-Glu-Ala-Glu-

Ala-Arg-Gly-Lys-Arg-Glu-Gly-Thr-Phe-Thr-Ser-Asp-

Val-Ser-Ser-Tyr-Leu-Glu-Gly-Gln-Ala-Ala-Lys-Glu-

Phe-Ile-Ala-Trp-Leu-Val-Arg-Gly-Arg-Gly-Lys-Arg-

Glu-Gly-Thr-Phe-Thr-Ser-Asp-Val-Ser-Ser-Tyr-Leu-

Glu-Gly-Gln-Ala-Ala-Lys-Glu-Phe-Ile-Ala-Trp-Leu-

Val-Arg-Gly-Arg-Gly-Lys-Arg-Glu-Gly-Thr-Phe-Thr-

Ser-Asp-Val-Ser-Ser-Tyr-Leu-Glu-Gly-Gln-Ala-Ala-

Lys-Glu-Phe-Ile-Ala-Trp-Leu-Val-Arg-Gly-Arg-Gly-

Lys-Arg-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Arg-Gly-Arg-Gly-COOH
```

Figure 8:
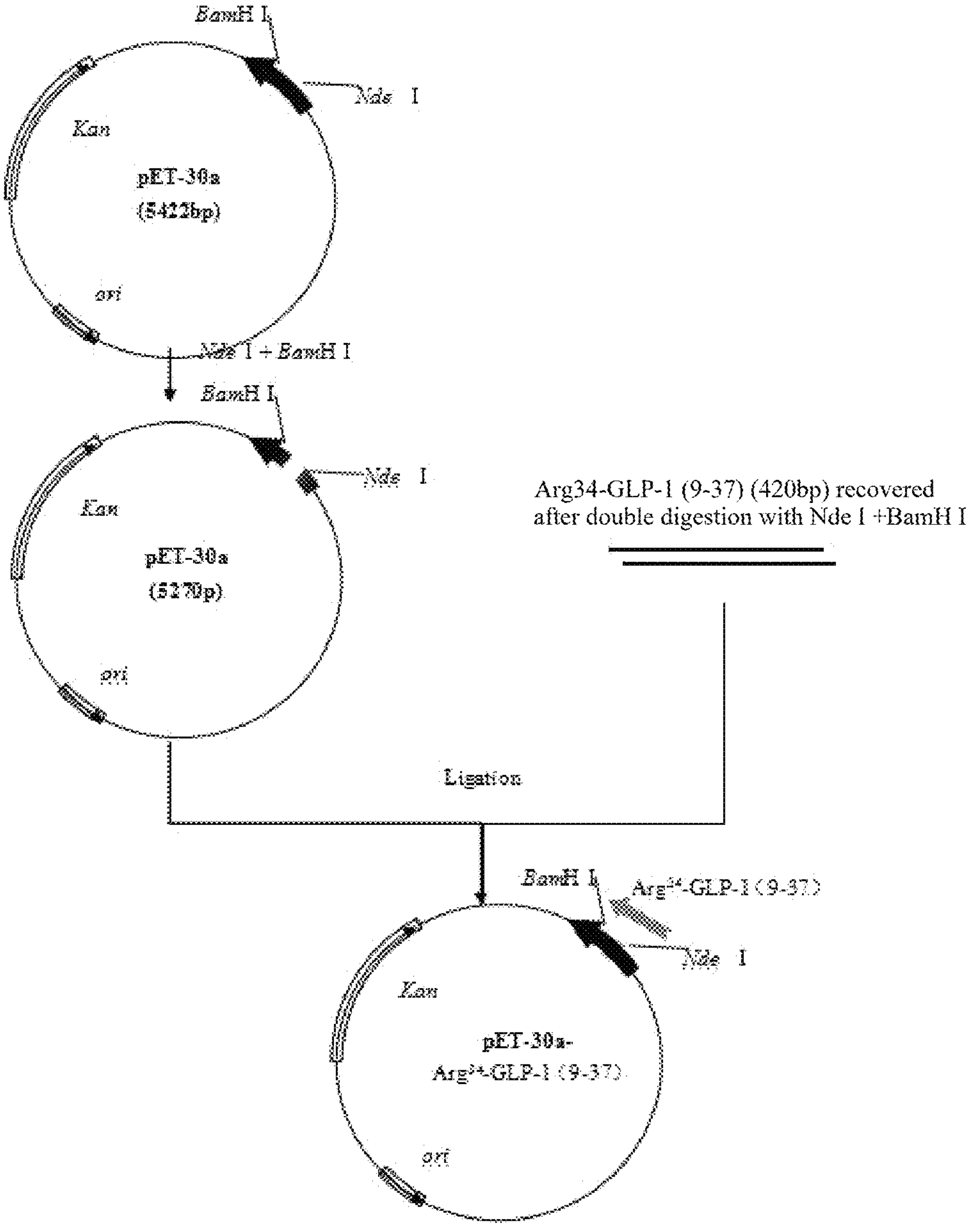
FIG. 8 is a schematic diagram of construction of recombinant plasmid pET-30a-$Arg^{34}$-GLP-1 (9-37) according to embodiments of the present disclosure.
Figure 9:
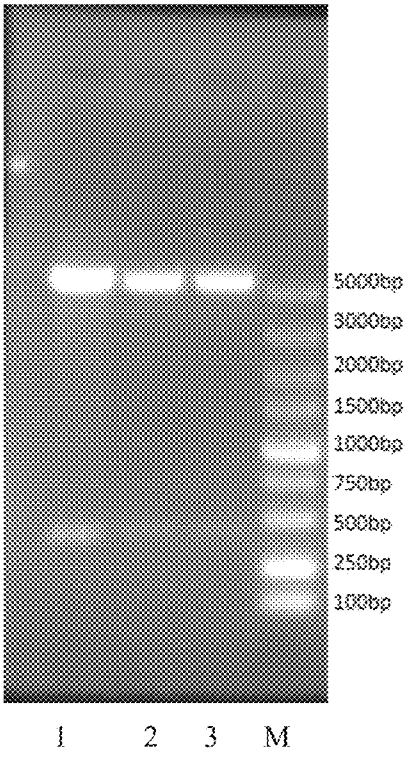
FIG. 9 is a diagram of identification of digestion of pET-30a-$Arg^{34}$-GLP-1 (9-37) according to embodiments of the present disclosure.

The recombinant plasmid PUC-57-Arg$^{34}$-GLP-1 (9-37) was double digested with Nde I/BamH I endonucleases and the target nucleotide sequences were recovered. The target nucleotide sequences were subsequently connected to Nde I/BamH I double-digested plasmid pET-30a (purchased from Novagen) via the T4 DNA ligase. Recombinant plasmids were transformed into the cloning host strain *E. coli* Top10, followed by enzyme digestion and PCR verification to screen the recombinant plasmid pET-30a-Arg$^{34}$-GLP-1 (9-37). After that, the cDNA sequence of Arg$^{34}$-GLP-1 (9-37) in the recombinant plasmid was identified as the correct sequence via the DNA sequencing. The recombinant plasmid pET-30a-Arg$^{34}$-GLP-1 (9-37) was transformed to the expression host strain *Escherichia coli* BL21 (DE3) and engineered recombinant bacteria were obtained via expression screening. A schematic diagram of construction of the recombinant plasmid is shown in FIG. 8. A diagram of identification of digestion of the recombinant plasmid is shown in FIG. 9, in which bands of about 5000 bp and 400 bp both appear after digestion regarding plasmids 1-3, corresponding to pET-30a and Arg$^{34}$-GLP-1 (9-37) respectively and consistent with theoretical values, indicating that Arg$^{34}$-GLP-1 (9-37) is correctly connected to the vector pET-30a.

Example 3 Construction of pET-30a-Arg$^{34}$-GLP-1 (11-37) Recombinant Plasmid and Engineered Recombinant Bacteria According to auxiliary peptide segment-(enzyme cleavage site-target protein sequence-enzyme cleavage site-target protein sequence)$_4$, Arg$^{34}$-GLP-1 (11-37) (SEQ ID NO: 3) repeats were connected in series and formed the sequence shown in SEQ ID NO: 15. The cDNA sequence shown in SEQ ID NO: 9 was designed based on the codon preference of *E. coli* and by adding the Nde I nuclease cleavage site CAT ATG at the 5' end, adding the double stop codons TAA TGA at the 3' end and adding the BamH I nuclease cleavage site GGA TCC. The nucleotide sequence was artificially whole gene synthesized, followed by construction on the PUC-57 vector to obtain a recombinant plasmid PUC-57-$Arg^{34}$-GLP-1 (11-37), which was transformed in *E. coli* bacteria Top10 Glycerol Stock for storage.

(SEQ ID NO: 15)

$NH_2$-Met-His-His-His-His-Glu-Glu-Ala-Glu-Ala-Glu-
Ala-Arg-Gly-Lys-Arg-Thr-Phe-Thr-Ser-Asp-Val-Ser-
Ser-Tyr-Leu-Glu-Gly-Gln-Ala-Ala-Lys-Glu-Phe-Ile-
Ala-Trp-Leu-Val-Arg-Gly-Arg-Gly-Lys-Arg-Thr-Phe-
Thr-Ser-Asp-Val-Ser-Ser-Tyr-Leu-Glu-Gly-Gln-Ala-
Ala-Lys-Glu-Phe-Ile-Ala-Trp-Leu-Val-Arg-Gly-Arg-
Gly-Lys-Arg-Thr-Phe-Thr-Ser-Asp-Val-Ser-Ser-Tyr-
Leu-Glu-Gly-Gln-Ala-Ala-Lys-Glu-Phe-Ile-Ala-Trp-
Leu-Val-Arg-Gly-Arg-Gly-Lys-Arg-Thr-Phe-Thr-Ser-
Asp-Val-Ser-Ser-Tyr-Leu-Glu-Gly-Gln-Ala-Ala-Lys-
Glu-Phe-Ile-Ala-Trp-Leu-Val-Arg-Gly-Arg-Gly-COOH

Figure 10:
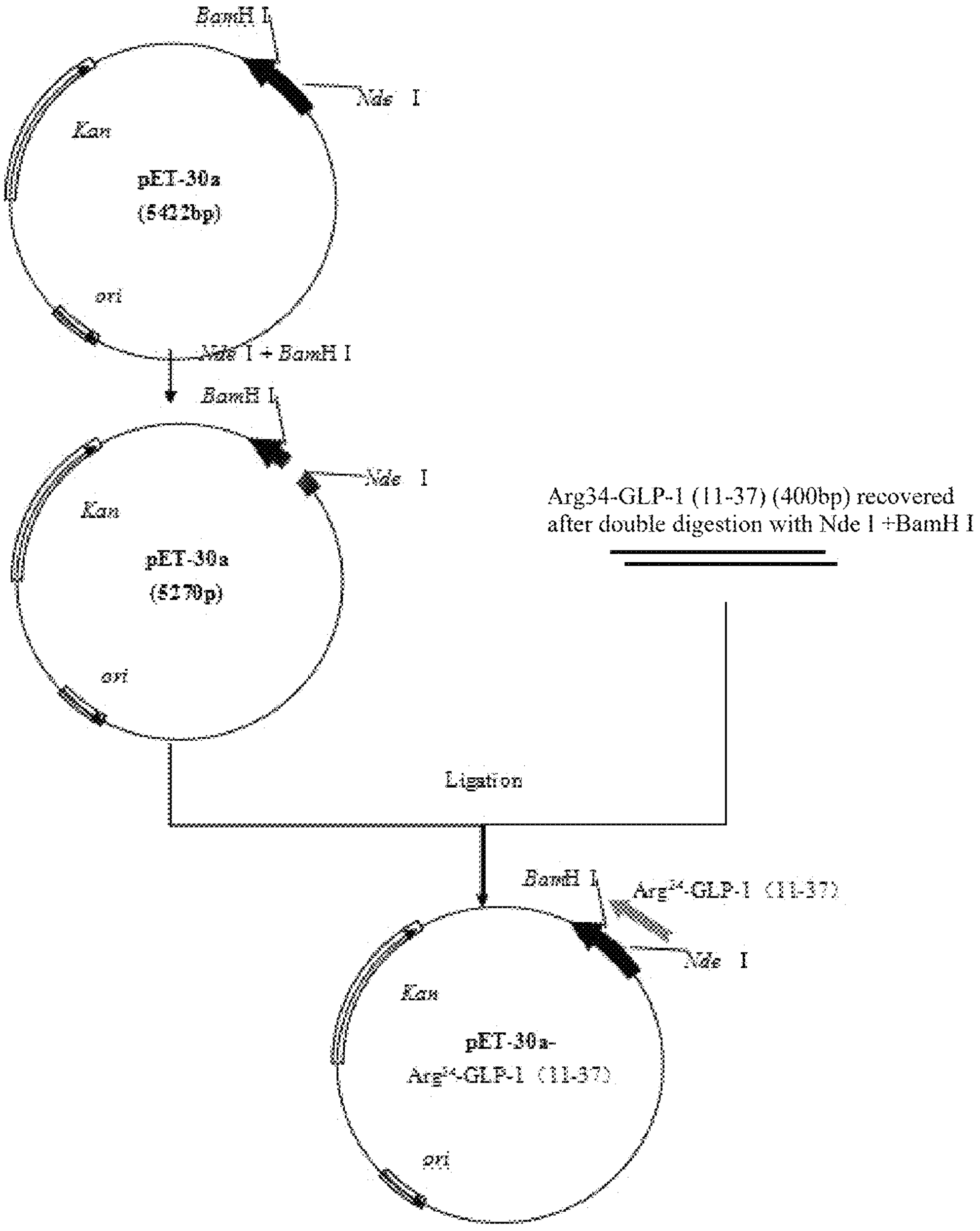
FIG. 10 is a schematic diagram of construction of recombinant plasmid pET-30a-$Arg^{34}$-GLP-1 (11-37) according to embodiments of the present disclosure.
Figure 11:
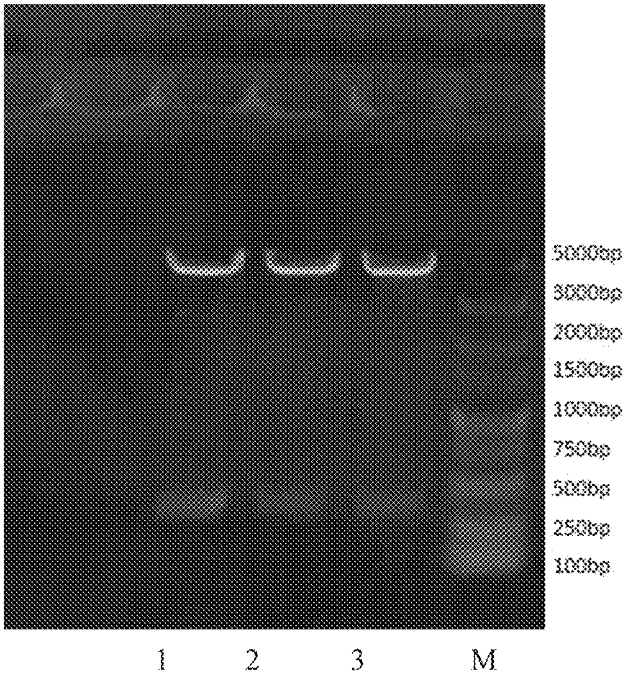
FIG. 11 is a diagram of identification of digestion of pET-30a-$Arg^{34}$-GLP-1 (11-37) according to embodiments of the present disclosure.

The recombinant plasmid PUC-57-$Arg^{34}$-GLP-1 (11-37) was double digested with Nde I/BamH I endonucleases and the target nucleotide sequences were recovered. The target nucleotide sequences were subsequently connected to Nde I/BamH I double-digested plasmid pET-30a (purchased from Novagen) via the T4 DNA ligase. Recombinant plasmids were transformed into the cloning host strain *E. coli* Top10, followed by enzyme digestion and PCR verification to screen the recombinant plasmid pET-30a-$Arg^{34}$-GLP-1 (11-37). After that, the cDNA sequence of $Arg^{34}$-GLP-1 (11-37) in the recombinant plasmid was identified as the correct sequence via the DNA sequencing. The recombinant plasmid pET-30a-$Arg^{34}$-GLP-1 (11-37) was transformed to the expression host strain *Escherichia coli* BL21 (DE3) and engineered recombinant bacteria were obtained via expression screening. A schematic diagram of construction of the recombinant plasmid is shown in FIG. 10. A diagram of identification of digestion of the recombinant plasmid is shown in FIG. 11, in which bands of about 5000 bp and 400 bp both appear after digestion regarding plasmids 1-3, corresponding to pET-30a and $Arg^{34}$-GLP-1 (11-37) respectively and consistent with theoretical values, indicating that $Arg^{34}$-GLP-1 (11-37) is correctly connected to the vector pET-30a.

Example 4 Construction of pET-30a-GLP-2 Recombinant Plasmid and Engineered Recombinant Bacteria According to auxiliary peptide segment-(enzyme cleavage site-target protein sequence-enzyme cleavage site-target protein sequence)$_4$, GLP-2 (SEQ ID NO: 4) repeats were connected in series and formed the sequence shown in SEQ ID NO: 16. The cDNA sequence shown in SEQ ID NO: 10 was designed based on the codon preference of *E. coli* and by adding the Nde I nuclease cleavage site CAT ATG at the 5' end, adding the double stop codons TAA TGA at the 3' end and adding the BamH I nuclease cleavage site GGA TCC. The nucleotide sequence was artificially whole gene synthesized, followed by construction on the PUC-57 vector to obtain a recombinant plasmid PUC-57-GLP-2, which was transformed in *E. coli* bacteria Top10 Glycerol Stock for storage.

(SEQ ID NO: 16)

$NH_2$-Met-His-His-His-His-Glu-Glu-Ala-Glu-Ala-Glu-
Ala-Arg-Gly-Lys-Arg-His-Gly-Asp-Gly-Ser-Phe-Ser-
Asp-Glu-Met-Asn-Thr-Ile-Leu-Asp-Asn-Leu-Ala-Ala-
Arg-Asp-Phe-Ile-Asn-Trp-Leu-Ile-Gln-Thr-Lys-Ile-
Thr-Asp-Arg-Lys-Arg-His-Gly-Asp-Gly-Ser-Phe-Ser-
Asp-Glu-Met-Asn-Thr-Ile-Leu-Asp-Asn-Leu-Ala-Ala-
Arg-Asp-Phe-Ile-Asn-Trp-Leu-Ile-Gln-Thr-Lys-Ile-
Thr-Asp-Arg-Lys-Arg-His-Gly-Asp-Gly-Ser-Phe-Ser-
Asp-Glu-Met-Asn-Thr-Ile-Leu-Asp-Asn-Leu-Ala-Ala-
Arg-Asp-Phe-Ile-Asn-Trp-Leu-Ile-Gln-Thr-Lys-Ile-
Thr-Asp-Arg-Lys-Arg-His-Gly-Asp-Gly-Ser-Phe-Ser-
Asp-Glu-Met-Asn-Thr-Ile-Leu-Asp-Asn-Leu-Ala-Ala-
Arg-Asp-Phe-Ile-Asn-Trp-Leu-Ile-Gln-Thr-Lys-Ile-
Thr-Asp-COOH

Figure 12:
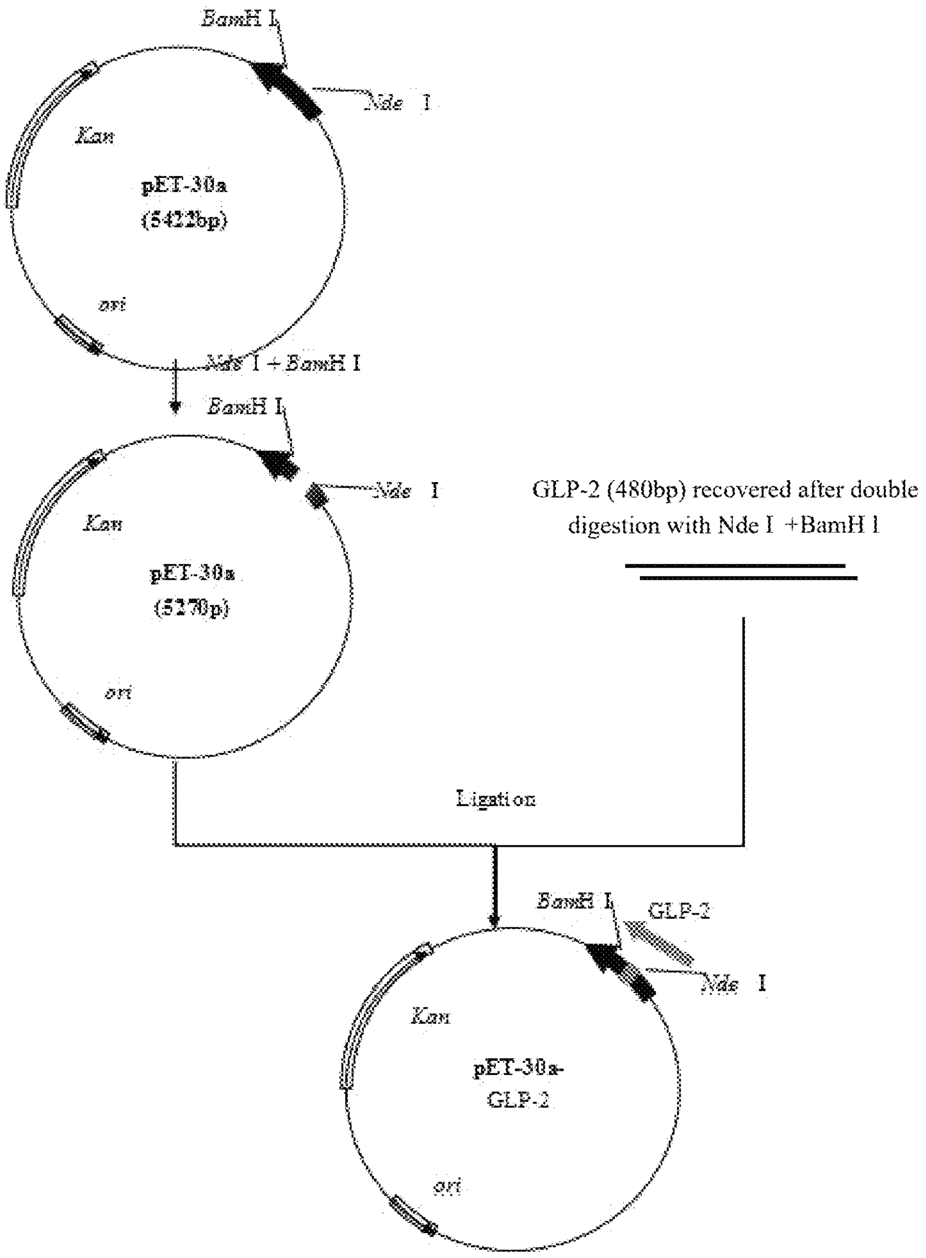
FIG. 12 is a schematic diagram of construction of recombinant plasmid pET-30a-GLP-2 according to embodiments of the present disclosure.
Figure 13:
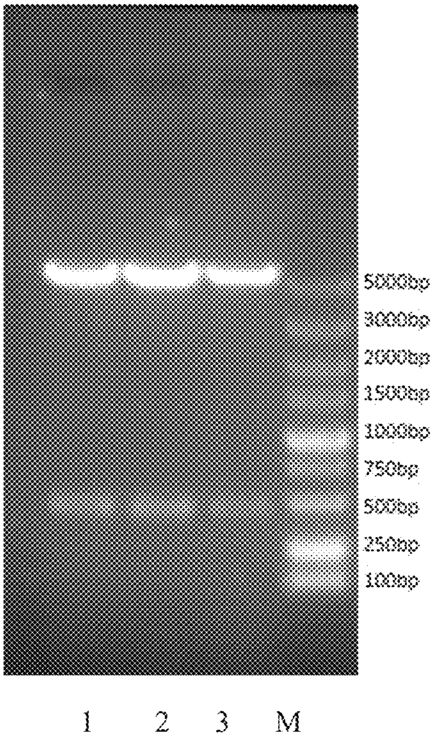
FIG. 13 is a diagram of identification of digestion of pET-30a-GLP-2 according to embodiments of the present disclosure.

The recombinant plasmid PUC-57-GLP-2 was double digested with Nde I/BamH I endonucleases and the target nucleotide sequences were recovered. The target nucleotide sequences were subsequently connected to Nde I/BamH I double-digested plasmid pET-30a (purchased from Novagen) via the T4 DNA ligase. Recombinant plasmids were transformed into the cloning host strain *E. coli* Top10, followed by enzyme digestion and PCR verification to screen the recombinant plasmid pET-30a-GLP-2. After that, the cDNA sequence of GLP-2 in the recombinant plasmid was identified as the correct sequence via the DNA sequencing. The recombinant plasmid pET-30a-GLP-2 was transformed to the expression host strain *Escherichia coli* $BL_{21}$ (DE3) and engineered recombinant bacteria were obtained via expression screening. A schematic diagram of construction of the recombinant plasmid is shown in FIG. 12. A diagram of identification of digestion of the recombinant plasmid is shown in FIG. 13, in which bands of about 5000 bp and 480 bp both appear after digestion regarding plasmids 1-3, corresponding to pET-30a and GLP-2 respectively and consistent with theoretical values, indicating that GLP-2 is correctly connected to the vector pET-30a.

Example 5 Construction of pET-30a-Glucagon Recombinant Plasmid and Engineered Recombinant Bacteria According to auxiliary peptide segment-(enzyme cleavage site-target protein sequence-enzyme cleavage site-target protein sequence)$_8$, Glucagon (SEQ ID NO: 5) repeats were connected in series and formed the sequence shown in SEQ ID NO: 17. The cDNA sequence shown in SEQ ID NO: 11 was designed based on the codon preference of *E. coli* and by adding the Nde I nuclease cleavage site CAT ATG at the 5' end, adding the double stop codons TAA TGA at the 3' end and adding the BamH I nuclease cleavage site GGA TCC. The nucleotide sequence was artificially whole gene synthesized, followed by construction on the PUC-57 vector to obtain a recombinant plasmid PUC-57-Glucagon, which was transformed in *E. coli* bacteria Top10 Glycerol Stock for storage.

(SEQ ID NO: 17)

```
NH2-Met-His-His-His-His-Glu-Glu-Ala-Glu-Ala-Glu-
Ala-Arg-Gly-Lys-Arg-His-Ser-Gln-Gly-Thr-Phe-Thr-
Ser-Asp-Tyr-Ser-Lys-Tyr-Leu-Asp-Ser-Arg-Arg-Ala-
Gln-Asp-Phe-Val-Gln-Trp-Leu-Met-Asn-Thr-Arg-Lys-
Arg-His-Ser-Gln-Gly-Thr-Phe-Thr-Ser-Asp-Tyr-Ser-
Lys-Tyr-Leu-Asp-Ser-Arg-Arg-Ala-Gln-Asp-Phe-Val-
Gln-Trp-Leu-Met-Asn-Thr-Arg-Lys-Arg-His-Ser-Gln-
Gly-Thr-Phe-Thr-Ser-Asp-Tyr-Ser-Lys-Tyr-Leu-Asp-
Ser-Arg-Arg-Ala-Gln-Asp-Phe-Val-Gln-Trp-Leu-Met-
Asn-Thr-Arg-Lys-Arg-His-Ser-Gln-Gly-Thr-Phe-Thr-
Ser-Asp-Tyr-Ser-Lys-Tyr-Leu-Asp-Ser-Arg-Arg-Ala-
Gln-Asp-Phe-Val-Gln-Trp-Leu-Met-Asn-Thr-Arg-Lys-
Arg-His-Ser-Gln-Gly-Thr-Phe-Thr-Ser-Asp-Tyr-Ser-
Lys-Tyr-Leu-Asp-Ser-Arg-Arg-Ala-Gln-Asp-Phe-Val-
Gln-Trp-Leu-Met-Asn-Thr-Arg-Lys-Arg-His-Ser-Gln-
Gly-Thr-Phe-Thr-Ser-Asp-Tyr-Ser-Lys-Tyr-Leu-Asp-
Ser-Arg-Arg-Ala-Gln-Asp-Phe-Val-Gln-Trp-Leu-Met-
Asn-Thr-Arg-Lys-Arg-His-Ser-Gln-Gly-Thr-Phe-Thr-
Ser-Asp-Tyr-Ser-Lys-Tyr-Leu-Asp-Ser-Arg-Arg-Ala-
Gln-Asp-Phe-Val-Gln-Trp-Leu-Met-Asn-Thr-Arg-Lys-
Arg-His-Ser-Gln-Gly-Thr-Phe-Thr-Ser-Asp-Tyr-Ser-
Lys-Tyr-Leu-Asp-Ser-Arg-Arg-Ala-Gln-Asp-Phe-Val-
Gln-Trp-Leu-Met-Asn-Thr-COOH
```

Figure 14:
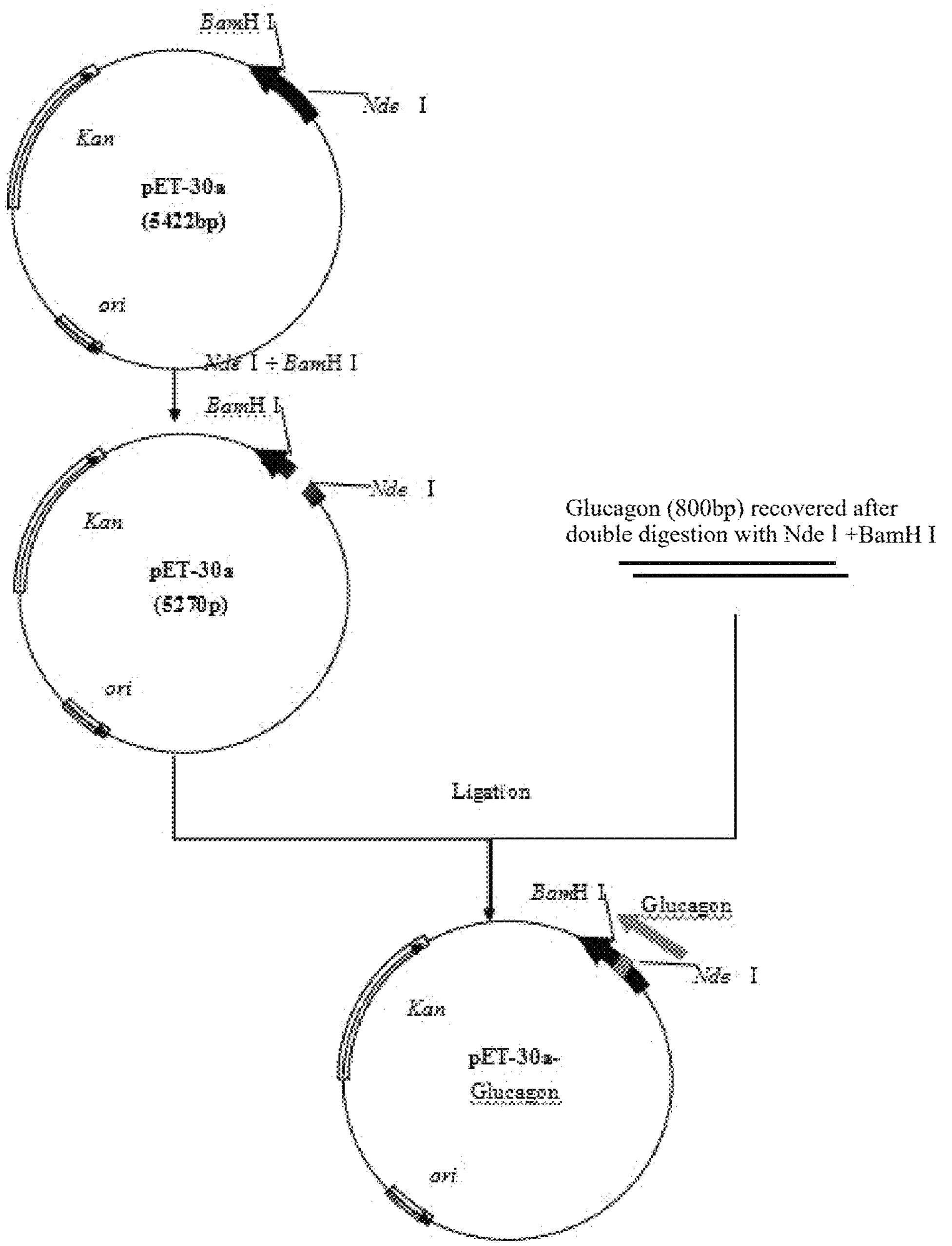
FIG. 14 is a schematic diagram of construction of recombinant plasmid pET-30a-Glucagon according to embodiments of the present disclosure.
Figure 15:
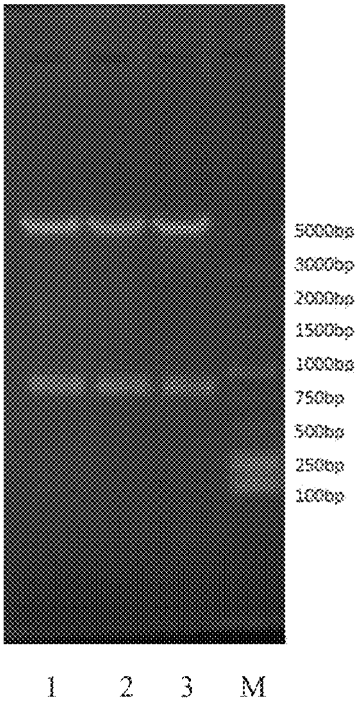
FIG. 15 is a diagram of identification of digestion of pET-30a-Glucagon according to embodiments of the present disclosure.

The recombinant plasmid PUC-57-Glucagon was double digested with Nde I/BamH I endonucleases and the target nucleotide sequences were recovered. The target nucleotide sequences were subsequently connected to Nde I/BamH I double-digested plasmid pET-30a (purchased from Novagen) via the T4 DNA ligase. Recombinant plasmids were transformed into the cloning host strain *E. coli* Top10, followed by enzyme digestion and PCR verification to screen the recombinant plasmid pET-30a-Glucagon. After that, the cDNA sequence of Glucagon in the recombinant plasmid was identified as the correct sequence via the DNA sequencing. The recombinant plasmid pET-30a-Glucagon was transformed to the expression host strain *Escherichia coli* $BL_{21}$ (DE3) and engineered recombinant bacteria were obtained via expression screening. A schematic diagram of construction of the recombinant plasmid is shown in FIG. 14. A diagram of identification of digestion of the recombinant plasmid is shown in FIG. 15, in which bands of about 5000 bp and 800 bp both appear after digestion regarding plasmids 1-3, corresponding to pET-30a and Glucagon respectively and consistent with theoretical values, indicating that Glucagon is correctly connected to the vector pET-30a.

Example 6 Construction of pET-30a-TB4 Recombinant Plasmid and Engineered Recombinant Bacteria According to auxiliary peptide segment-(enzyme cleavage site-target protein sequence-enzyme cleavage site-target protein sequence)$_4$, TB4 (SEQ ID NO: 6) repeats were connected in series and formed the sequence shown in SEQ ID NO: 18. The cDNA sequence shown in SEQ ID NO: 12 was designed based on the codon preference of *E. coli* and by adding the Nde I nuclease cleavage site CAT ATG at the 5' end, adding the double stop codons TAA TGA at the 3' end and adding the BamH I nuclease cleavage site GGA TCC. The nucleotide sequence was artificially whole gene synthesized, followed by construction on the PUC-57 vector to obtain a recombinant plasmid PUC-57-TB4, which was transformed in *E. coli* bacteria Top10 Glycerol Stock for storage.

(SEQ ID NO: 18)

```
NH2-Met-His-His-His-His-Glu-Glu-Ala-Glu-Ala-Glu-
Ala-Arg-Gly-Lys-Arg-Ser-Asp-Lys-Pro-Asp-Met-Ala-
Glu-Ile-Glu-Lys-Phe-Asp-Lys-Ser-Lys-Leu-Lys-Lys-
Thr-Glu-Thr-Gln-Glu-Lys-Asn-Pro-Leu-Pro-Ser-Lys-
Glu-Thr-Ile-Glu-Gln-Glu-Lys-Gln-Ala-Gly-Glu-Ser-
Arg-Lys-Arg-Ser-Asp-Lys-Pro-Asp-Met-Ala-Glu-Ile-
Glu-Lys-Phe-Asp-Lys-Ser-Lys-Leu-Lys-Lys-Thr-Glu-
Thr-Gln-Glu-Lys-Asn-Pro-Leu-Pro-Ser-Lys-Glu-Thr-
Ile-Glu-Gln-Glu-Lys-Gln-Ala-Gly-Glu-Ser-Arg-Lys-
Arg-Ser-Asp-Lys-Pro-Asp-Met-Ala-Glu-Ile-Glu-Lys-
Phe-Asp-Lys-Ser-Lys-Leu-Lys-Lys-Thr-Glu-Thr-Gln-
Glu-Lys-Asn-Pro-Leu-Pro-Ser-Lys-Glu-Thr-Ile-Glu-
Gln-Glu-Lys-Gln-Ala-Gly-Glu-Ser-Arg-Lys-Arg-Ser-
Asp-Lys-Pro-Asp-Met-Ala-Glu-Ile-Glu-Lys-Phe-Asp-
Lys-Ser-Lys-Leu-Lys-Lys-Thr-Glu-Thr-Gln-Glu-Lys-
Asn-Pro-Leu-Pro-Ser-Lys-Glu-Thr-Ile-Glu-Gln-Glu-
Lys-Gln-Ala-Gly-Glu-Ser-COOH
```

Figure 16:
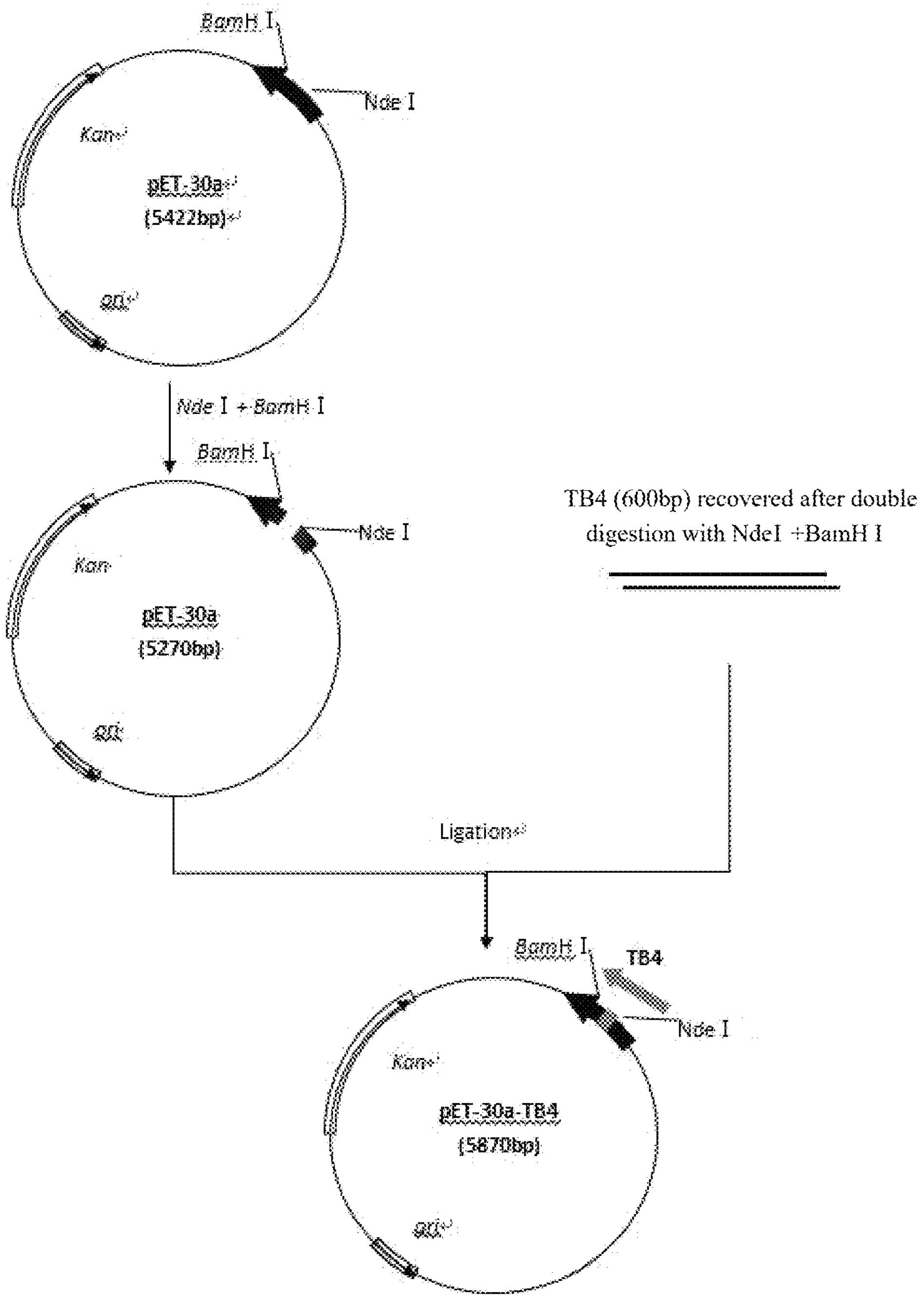
FIG. 16 is a schematic diagram of construction of recombinant plasmid pET-30a-T4B according to embodiments of the present disclosure.
Figure 17:
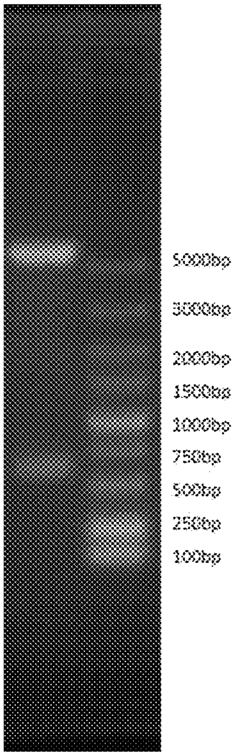
FIG. 17 is a diagram of identification of digestion of pET-30a-T4B according to embodiments of the present disclosure.

The recombinant plasmid PUC-57-TB4 was double digested with Nde I/BamH I endonucleases and the target nucleotide sequences were recovered. The target nucleotide sequences were subsequently connected to Nde I/BamH I double-digested plasmid pET-30a (purchased from Novagen) via the T4 DNA ligase. Recombinant plasmids were transformed into the cloning host strain *E. coli* Top10, followed by enzyme digestion and PCR verification to screen the recombinant plasmid pET-30a-TB4. After that, the cDNA sequence of TB4 in the recombinant plasmid was identified as the correct sequence via the DNA sequencing. The recombinant plasmid pET-30a-TB4 was transformed to the expression host strain *Escherichia coli* $BL_{21}$ (DE3) and engineered recombinant bacteria were obtained via expression screening. A schematic diagram of construction of the recombinant plasmid is shown in FIG. 16. A diagram of identification of digestion of the recombinant plasmid is shown in FIG. 17, in which bands of about 5000 bp and 600 bp both appear after digestion regarding plasmids, corresponding to pET-30a and TB4 respectively and consistent with theoretical values, indicating that TB4 is correctly connected to the vector pET-30a.

Example 7 Fermentation Culture of Engineered Recombinant Bacteria pET-30a-$Arg^{34}$-GLP-1(7-37)/$BL_{21}$(DE3), pET-30a-$Arg^{34}$-GLP-1(9-37)/$BL_{21}$(DE3), pET-30a-$Arg^{34}$-GLP-1(11-37)/$BL_{21}$(DE3), pET-30a-GLP-2/$BL_{21}$(DE3), pET-30a-Glucagon/$BL_{21}$(DE3), pET-30a-TB4/BL21(DE3)

Engineered recombinant bacteria pET-30a-$Arg^{34}$-GLP-1 (7-37)/$BL_{21}$(DE3), pET-30a-$Arg^{34}$-GLP-1(9-37)/$BL_{21}$(DE3), pET-30a-$Arg^{34}$-GLP-1(11-37)/$BL_{21}$(DE3), pET-30a-GLP-2/$BL_{21}$(DE3), pET-30a-Glucagon/$BL_{21}$(DE3) and pET-30a-TB4/$BL_{21}$(DE3) were respectively streak plated on LA agar plates and incubated overnight at 37° C. Bacterial lawn was picked from the cultured LA agar plates and inoculated in liquid LB culture medium, followed by culturing at 37° C. for 12 hours. The bacterial solution was transferred to a 1000 ml conical flask containing 200 ml LB medium at a ratio of 1% and cultured overnight at 37° C. to harvest seed liquid for fermentation tank. The seed liquid was inoculated in a 30L fermentation tank containing YT culture medium at a ratio of 5% and cultured at 37° C. During the fermentation culture, the dissolved oxygen was kept at above 25% by adjusting rotation speed, air volume and pure oxygen volume and the pH was maintained at 6.5 by adding ammonia water. When the $OD_{600}$ of the bacterial solution reaches a value of 50 to 80, isopropyl-β-D-thiogalactoside with a final concentration of 0.2 mM was added. The fermentation culture was continued for another 3 hours until stopping the culture. The bacterial solution was collected and centrifuged at 8000 rpm for 10 minutes. The supernatant was discarded and the bacterial cell pellet was collected and stored in a refrigerator at −20° C. for use.

Figure 18:
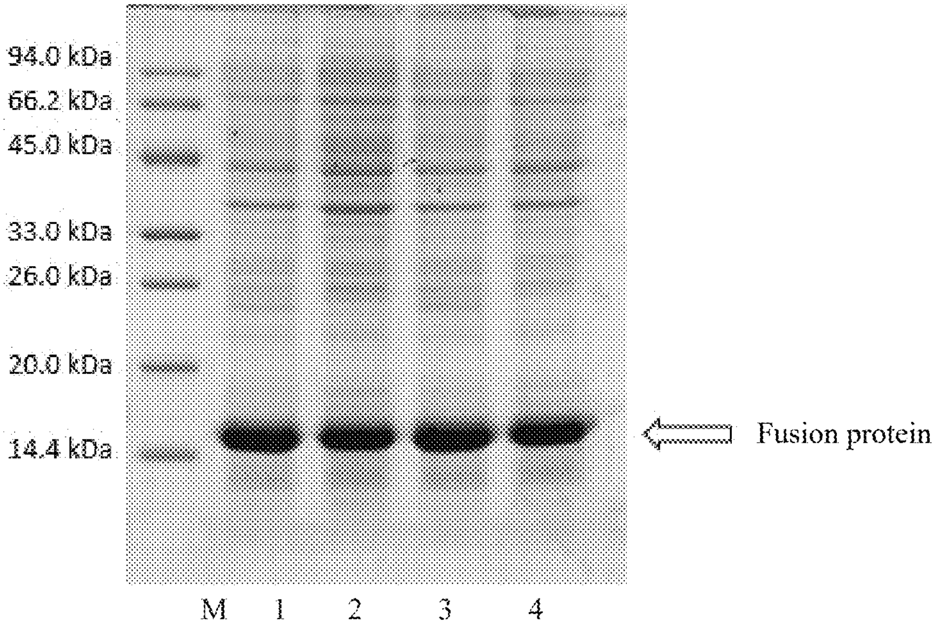
FIG. 18 is a diagram showing SDS-PAGE results of induced expression of engineered recombinant bacteria pET-30a-$Arg^{34}$-GLP-1 (9-37)/BL21(DE3) according to embodiments of the present disclosure.

Among them, the SDS-PAGE diagram of induced expression of engineered recombinant bacteria pET-30a-$Arg^{34}$-GLP-1 (9-37)/$BL_{21}$(DE3) is shown in FIG. 18.

Example 8 Pretreatment, Enzyme Digestion and Purification of $Arg^{34}$-GLP-1 (9-37)

The cell pellet of engineered recombinant bacteria pET-30a-$Arg^{34}$-GLP-1 (9-37)/$BL_{21}$(DE3) after fermentation culture were suspended in a crushing buffer, homogenized at a high pressure of 600 to 700 Bar three times, stirred at room temperature and centrifuged to collect a precipitate. The precipitate was suspended in a washing liquid via a ratio of mass to volume, homogenized with a homogenizer until no particle was visible. The homogeneous mixture was stirred at room temperature for 30 minutes and centrifuged to collect a precipitate, which was dissolved in an enzyme digestion buffer containing a surfactant at a mass/volume ratio of 3% to 5% by g/mL. The mixture was adjusted to a pH value of 10.5, stirred for 30 minutes at 28° C. to 32° C. and centrifuged to collect a supernatant. The content of the fusion protein expressed in the recombinant bacteria was determined by $OD_{280}$ ultraviolet. The supernatant containing the fusion protein was adjusted to a pH value of 8.0 to 9.0 and the recombinant proteases Kex2 and CPB were added at the mass ratio (the protease to the fusion protein) of 1:1000, followed by enzyme digestion reaction at 25° C. to 35° C. under stirring overnight. The enzyme digestion product was detected through the RP-HPLC method, in which the Q anion chromatography column was routinely cleaned, regenerated and equilibrated with a balance solution to 2CV. The enzyme digestion product adjusted to a pH value of 9.5 to 9.8 was loaded to the Q anion chromatography column with a conductivity lower than 5 ms/cm, rebalanced to 1CV, eluted with a first eluent until the ultraviolet absorption value was reset to zero, equilibrated with a balance solution to 2CV, followed by eluted with a second eluent to collect a liquid containing the target peak. The collected liquid was loaded to the C4 reversed-phase column, equilibrated, eluted in gradients to collect the target protein sequences, with the purity of 99% or above.

Figure 19:
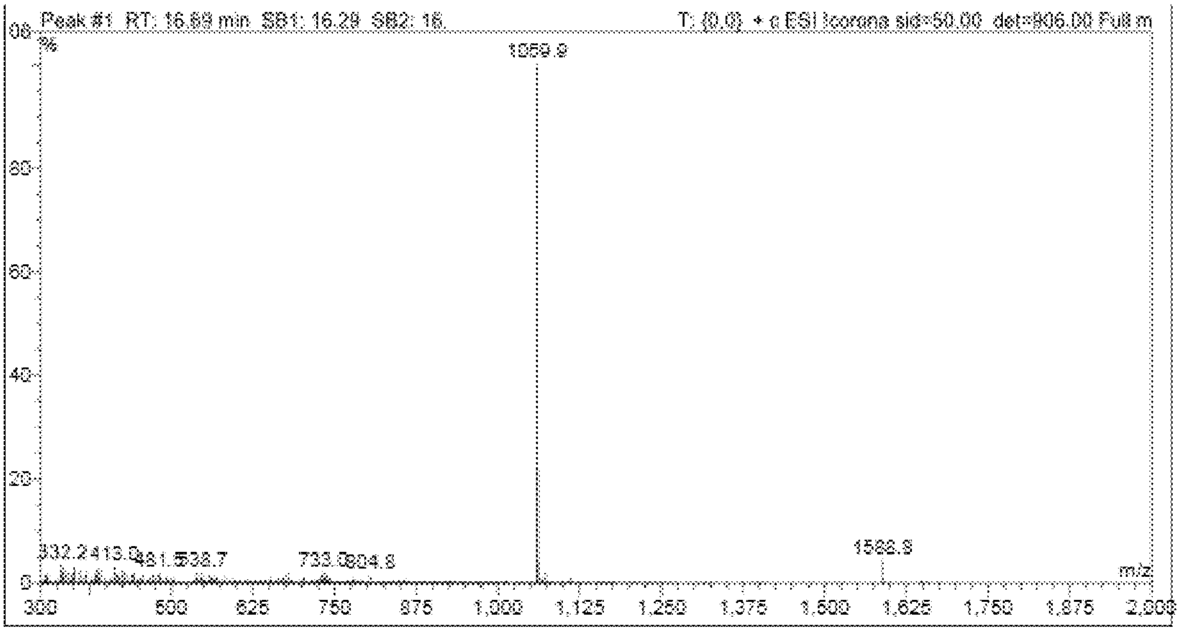
FIG. 19 is a mass spectrum showing molecular weights of $Arg^{34}$-GLP-1 (9-37) after digestion according to embodiments of the present disclosure.

The mass spectrum of molecular weights of $Arg^{34}$-GLP-1 (9-37) after digestion is shown in FIG. 19.

Example 9 In Vitro Activity Assay of $Arg^{34}$-GLP-1 (9-37)

Figure 20:
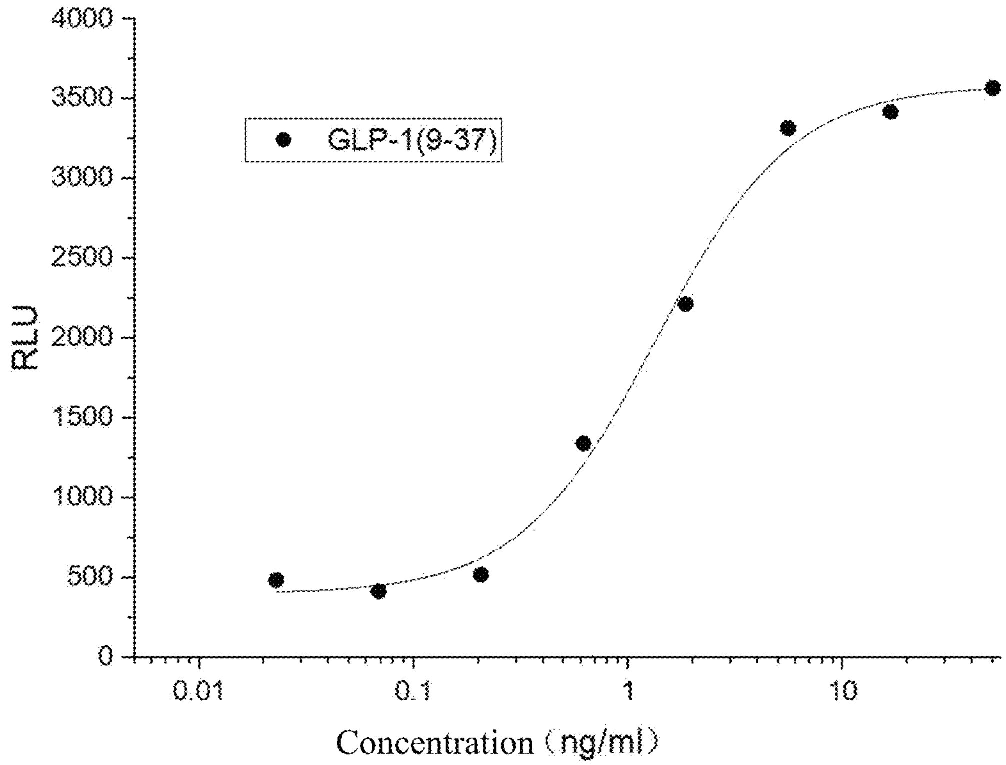
FIG. 20 is a graph showing the in vitro cellular biological activity of $Arg^{34}$-GLP-1 (9-37) according to embodiments of the present disclosure.

In vitro activity assay was conducted by using recombinant cells CHO-K1-CRE-GLP1R transfected with GLP-1R receptor from PEG-BIO BIOPHARM CO., LTD. The recombinant cells CHO-K1-CRE-GLP1R were plated overnight, followed by stimulation with the target protein $Arg^{34}$-GLP-1 (9-37), reacted under 5% $CO_2$ at 37° C. for 4 hours±15 minutes. A chemiluminescent substrate (Promega kit, Cat.: No. E2510) was added in an amount of 100 μl/well and gently shook on an oscillator for 40 minutes±10 minutes at room temperature. Each well in the plate was measured on the microplate reader in an appropriate time of 1 second/well for the relative luciferase unit (RLU). A four-parameter regression curve was fit by the "Sigmaplot" software to calculate the half-effect dose ($EC_{50}$) of $Arg^{34}$-GLP-1 (9-37). The result of in vitro activity of $Arg^{34}$-GLP-1 (9-37) is shown in FIG. 20.

Example 10 In Vitro Activity Assay of GLP-2

Figure 21:
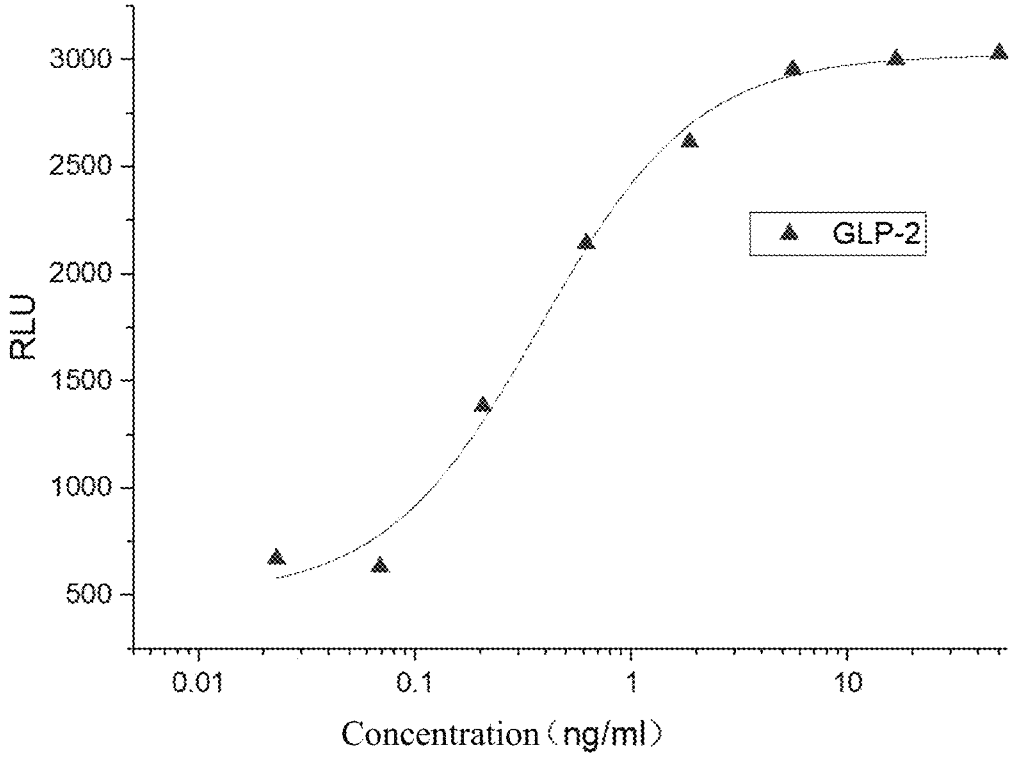
FIG. 21 is a graph showing the in vitro cellular biological activity of GLP-2 according to embodiments of the present disclosure.

In vitro activity assay was conducted by using recombinant cells CHO-K1-CRE-GLP2R transfected with GLP-2R receptor from PEG-BIO BIOPHARM CO., LTD. The recombinant cells CHO-K1-CRE-GLP2R were plated overnight, followed by stimulation with the target protein GLP-2, reacted under 5% $CO_2$ at 37° C. for 4 hours±15 minutes. A chemiluminescent substrate (Promega kit, Cat.: No. E2510) was added in an amount of 100 μl/well and gently shook on an oscillator for 40 minutes±10 minutes at room temperature. Each well in the plate was measured on the microplate reader in an appropriate time of 1 second/well for the relative luciferase unit (RLU). A four-parameter regression curve was fit by the "Sigmaplot" software to calculate the half-effect dose ($EC_{50}$) of GLP-2. The result of in vitro activity of GLP-2 is shown in FIG. 21.

Some illustrative experimental schemes conducted during the development of the present method were also described to show the advantage of the present method. The experimental method and results are presented in the below examples, which show that the present method achieves significantly better effects compared to the method in the comparative examples.

Comparative Example 1

Different expression promoting sequences in the auxiliary peptide segment of the fusion protein were investigated in the development of the present method to effectively increase the expression level of the fusion protein. The screening process was described in detail as below.

The fusion proteins containing the expression promoting sequence EEAEAEARG (SEQ ID NO: 21) and the fusion proteins not containing the expression promoting sequence EEAEAEARG (SEQ ID NO: 21) were designed and induced to express by fermentation culture, followed by enzyme cleavage to obtain the target protein sequences. The results are as follows.

Figure 22:
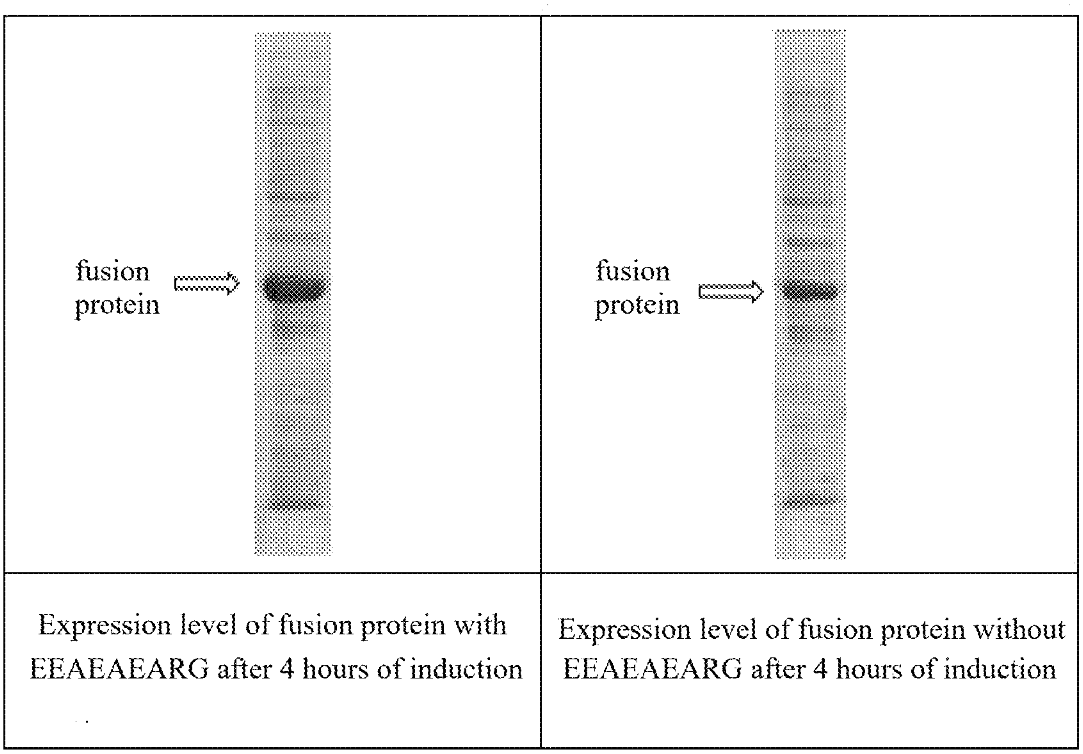
FIG. 22 is a diagram of comparison of induced expression levels of fusion proteins with or without a promoting expression peptide (EEAEAEARG) (SEQ ID NO: 21) according to embodiments of the present disclosure.

(a) The expression levels of fusion proteins containing or not containing the promoting expression peptide EEAEAEARG (SEQ ID NO: 21) is shown in FIG. 22.

Conclusion: the fusion proteins containing EEAEAEARG (SEQ ID NO: 21) exhibit a higher expression level than that of the fusion proteins not containing EEAEAEARG (SEQ ID NO: 21) after 4 hours of induction.

Figure 23:
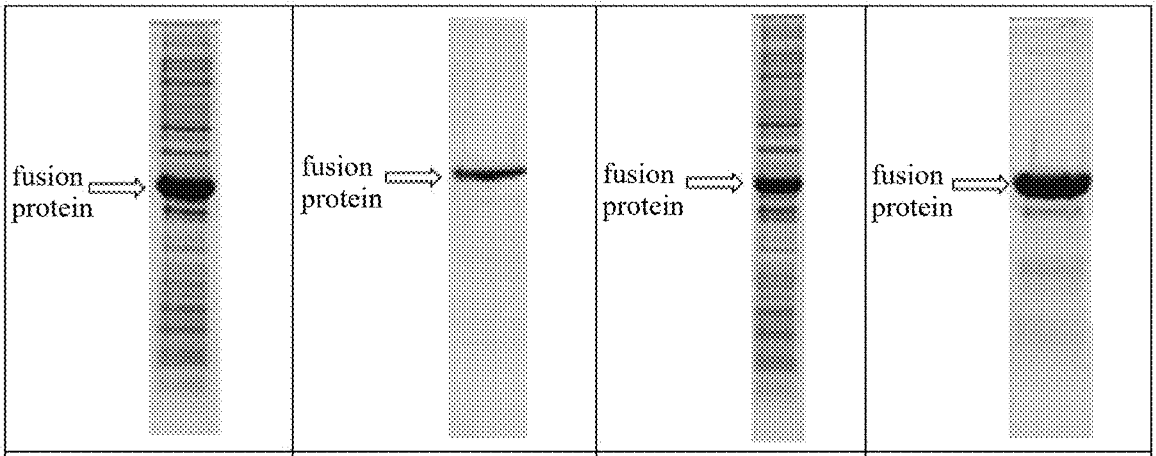
FIG. 23 is a diagram of comparison of fusion protein contents in the supernatant of crushed bacteria expressing or not expressing a promoting expression peptide (EEAEAEARG) (SEQ ID NO: 21) according to embodiments of the present disclosure.

(b) The solubility of fusion proteins containing or not containing the promoting expression peptide EEAEAEARG (SEQ ID NO: 21) is shown in FIG. 23.

Conclusion: The fusion protein content in the supernatant of crushed bacteria expressing the promoting expression peptide EEAEAEARG (SEQ ID NO: 21) is higher than the fusion protein content in the supernatant of crushed bacteria not expressing the promoting expression peptide EEAEAEARG (SEQ ID NO: 21).

Figure 24:
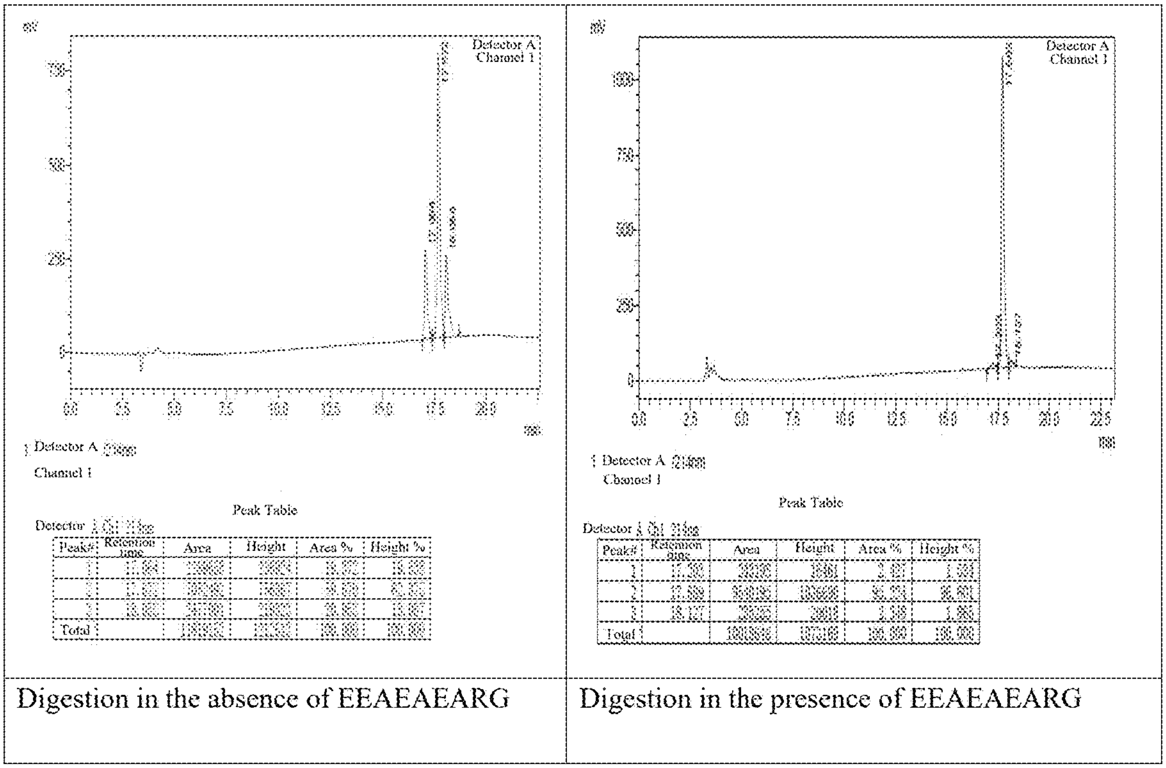
FIG. 24 is a diagram of comparison of enzyme cleavage efficiency of fusion proteins with or without a promoting expression peptide (EEAEAEARG) (SEQ ID NO: 21) according to embodiments of the present disclosure.

(c) Enzyme cleavage efficiency of fusion proteins containing or not containing the promoting expression peptide EEAEAEARG (SEQ ID NO: 21) is shown in FIG. 24.

Conclusion: the enzyme cleavage efficiency of fusion protein containing EEAEAEARG (SEQ ID NO: 21) is 96.6%, while the enzyme cleavage efficiency of fusion protein not containing EEAEAEARG (SEQ ID NO: 21) is 62.3%, indicating the fusion protein containing EEAEAEARG (SEQ ID NO: 21) has a higher cleavage efficiency than that of the fusion protein not containing EEAEAEARG (SEQ ID NO: 21).

The introduced protease recognition sites KR are all basic amino acids, which greatly increases the isoelectric point of the fusion protein and in turn adversely affects the expression of the fusion protein and the solubility of the fusion protein in the subsequent purification. The acidic amino acid glutamic acid (E) in the expression promoting sequence EEAEAEARG (SEQ ID NO: 21) balances the isoelectric point of the fusion protein, thereby facilitating the increase of the expression of the fusion protein, improving the digestion efficiency of the fusion protein and increasing the yield of the target proteins.

In the description of this specification, reference to terms “an embodiment”, “some embodiments”, “one embodiment”, “an example”, “an illustrative example”, “some examples” or the like means that a particular feature, structure, material or characteristic described in connection with the embodiment or example is included in at least one embodiment or example of the present disclosure. Thus, the illustrative representations of the terms are not necessarily directed to the same embodiment or example in this specification. Moreover, the specific features, structures, materials or characteristics as described can be combined in any one or more embodiments or examples in a suitable manner. In addition, those skilled persons in the art can combine different embodiments or examples or the features of the different embodiments or examples described in this specification without contradicting each other.

Although the embodiments of the present disclosure have been shown and described above, it can be understood that the embodiments described above are exemplary and should not be construed as limiting the present disclosure. An ordinary skilled person in the art could make changes, modifications, substitutions and modifications to the embodiments within the scope of the present disclosure.

The invention claimed is:

1. A fusion protein, comprising a plurality of target protein sequences connected in series,
   - wherein every two adjacent target protein sequences are connected by a linker sequence,
   - the linker sequence is capable of being cleaved by a protease to form the plurality of the target protein sequences in a free form,
   - the plurality of the target protein sequences each are not cleaved by the protease, and
   - neither a C-terminus nor an N-terminus of the plurality of target protein sequences in the free form contains additional residues,
   - wherein the fusion protein further comprises an auxiliary peptide segment, wherein a carboxyl terminus of the auxiliary peptide segment is connected to the N-terminus of the plurality of the target protein sequences connected in series via the linker sequence,
   - wherein the auxiliary peptide segment comprises a tag sequence and an expression promoting sequence,
   - wherein the amino acid sequence of the expression promoting sequence consists of EEAEAEAGG (SEQ ID NO: 20) or consists of EEAEAEARG (SEQ ID NO: 21).

2. The fusion protein according to claim 1, wherein the linker sequence is composed of at least one protease recognition site,
   - the linker sequence has a length of 1 to 10 amino acids,
   - the fusion protein comprises a plurality of linker sequences and the plurality of the linker sequences are same or different.

3. The fusion protein according to claim 2, wherein the protease recognition site is consecutive lysine-arginine (KR) and the protease is Kex2 protease.

4. The fusion protein according to claim 1, wherein the linker sequence comprises a first protease recognition site and a second protease recognition site, and the plurality of the target protein sequences each do not comprise the second protease recognition site, wherein
   - the first protease recognition site is recognized and cleaved by a first protease to form a first protease cleavage product and the N-terminus of the first protease cleavage product does not carry any residue of the linker sequence, and
   - the second protease recognition site is recognized and cleaved by a second protease and the second protease is capable of cleaving the C-terminus of the first protease cleavage product to form the plurality of the target proteins sequences in the free form, wherein neither the C-terminus nor the N-terminus of the target protein sequence in the free form contains a residue of the linker sequence.

5. The fusion protein according to claim 4, wherein the plurality of the target protein sequences comprise at least one first internal protease recognition site,
   - a sequence before or after the first internal protease recognition site comprises a consecutive acidic amino acid sequence adjacent to the first internal protease recognition site, and
   - the first internal protease recognition site is not recognized by the first protease.

6. The fusion protein according to claim 5, wherein the first protease is Kex2 protease,
   - the first internal protease recognition site is at least one of lysine-lysine (KK) and arginine-lysine (RK), and
   - the first protease recognition site in the linker sequence is lysine-arginine (KR), arginine-arginine (RR) or arginine-lysine-arginine (RKR).

7. The fusion protein according to claim 5, wherein the consecutive acidic amino acid sequence is of a length of 1 to 2 amino acids, and wherein the acidic amino acid is aspartic acid or glutamic acid.

8. The fusion protein according to claim 7, wherein the plurality of the target protein sequences comprise consecutive aspartic acid-lysine-arginine (DKR), aspartic acid-arginine-arginine (DRR), aspartic acid-lysine-lysine (DKK) or aspartic acid-arginine-lysine (DRK),
   - the first protease recognition site is lysine-arginine (KR), arginine-arginine (RR) or arginine-lysine-arginine (RKR) and the second protease recognition site is the carboxyl terminal arginine (R) or lysine (K), and
   - the first protease is Kex2 protease and the second protease is carboxypeptidase B (CPB) protease.

9. The fusion protein according to claim 4, wherein the plurality of the target protein sequences do not comprise both the first protease recognition site and the second protease recognition site.

10. The fusion protein according to claim 4, wherein the first protease recognition site and the second protease recognition site have an overlapping domain.

11. The fusion protein according to claim 4, wherein the first protease recognition site and the second protease recognition site meet one of the following conditions:
   - the amino acid sequence of the target protein sequence does not have consecutive lysine-arginine (KR) or arginine-arginine (RR) and optionally does not have consecutive lysine-lysine (KK) or arginine-lysine (RK), the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease;
   - the amino acid sequence of the target protein sequence does not have lysine (K) and has arginine (R), the first protease recognition site is lysine (K) and the first protease is Lys-C protease, and the second protease recognition site is carboxyl terminal lysine (K) and the second protease is CPB protease;
   - the amino acid sequence of the target protein sequence does not have both lysine (K) and arginine (R), the first protease recognition site is lysine (K) or arginine (R) and the first protease is Lys-C or Trp protease, and the second protease recognition site is carboxyl terminal lysine (K) or arginine (R) and the second protease is CPB protease; and the amino acid sequence of the target protein sequence has consecutive lysine-arginine (KR), arginine-arginine (RR), lysine-lysine (KK) or arginine-lysine (RK) and the consecutive lysine-arginine (KR), arginine-arginine (RR), lysine-lysine (KK) or arginine-lysine (RK) is adjacent to 1 or 2 consecutive acidic amino acids, the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease.

12. The fusion protein according to claim 1, wherein the amino acid sequence of the tag sequence is a repeated histidine (His) sequence, the first amino acid of the auxiliary peptide segment is methionine (Met).

13. The fusion protein according to claim 1, wherein the target protein sequence is of a length of 10 to 100 amino acids, the target protein sequence is of an amino acid sequence as shown in any one of SEQ ID NOs: 1 to 6, the fusion protein comprises 4 to 16 target protein sequences connected in series.

14. A method for obtaining a target protein sequence in a free form according to claim 1, comprising:

providing a fusion protein of claim 1, contacting the fusion protein with a protease to obtain a plurality of the target protein sequences in the free form, wherein:

the protease is determined based on a linker sequence, the plurality of the target protein sequences each are not cleaved by the protease, and neither a C-terminus nor an N-terminus of the plurality of target protein sequences in the free form contains additional residues.

15. The method according to claim 14, wherein contacting the fusion protein with a protease further comprises:

contacting the fusion protein with a first protease to obtain a first protease cleavage product, wherein the N-terminus of the first protease cleavage product does not carry any residue of the linker sequence, contacting the first protease cleavage product with a second protease to obtain the plurality of target protein sequences in the free form, wherein the second protease is capable of cleaving the C-terminus of the first protease cleavage product, wherein the linker sequence comprises a first protease recognition site and a second protease recognition site, and the plurality of the target protein sequences each do not comprise the second protease recognition site.

16. The method according to claim 14, wherein the fusion protein is obtained by fermentation of a microorganism carrying a nucleic acid encoding the fusion protein, the microorganism is *Escherichia coli*.

17. The method according to claim 16, further comprising subjecting the fermentation product of the microorganism to crushing and dissolving, wherein the dissolving is performed in the presence of a detergent to obtain the fusion protein.

18. A fusion protein, comprising a plurality of target protein sequences connected in series, wherein every two adjacent target protein sequences are connected by a linker sequence, wherein the linker sequence comprises a first protease recognition site and a second protease recognition site, and the plurality of target protein sequences each do not comprise the first protease recognition site and the second protease recognition site, wherein the first protease recognition site is recognized and cleaved by a first protease and the second protease recognition site is recognized and cleaved by a second protease, wherein the first protease recognition site is lysine-arginine (KR), arginine-arginine (RR) or arginine-lysine-arginine (RKR) and the first protease is Kex2 protease, and the second protease recognition site is carboxyl terminal arginine (R) or lysine (K) and the second protease is CPB protease, the linker sequence is capable of being cleaved by the first and second protease to form the plurality of the target protein sequences in a free form, the plurality of the target protein sequences each are not cleaved by the protease, and neither a C-terminus nor an N-terminus of the plurality of target protein sequences in the free form contains additional residues, wherein the fusion protein further comprises an auxiliary peptide segment, wherein a carboxyl terminus of the auxiliary peptide segment is connected to the N-terminus of the plurality of the target protein sequences connected in series via the linker sequence, wherein the auxiliary peptide segment comprises a tag sequence and an expression promoting sequence, wherein the amino acid sequence of the expression promoting sequence consists of EEAEAEAGG (SEQ ID NO: 20) or consists of EEAEAEARG (SEQ ID NO: 21).

* * * * *

SEQUENCE LISTING

```
<160> NUMBER OF SEQ ID NOS: 21

<210> SEQ ID NO 1
<211> LENGTH: 31
<212> TYPE: PRT
<213> ORGANISM: Artificial Sequence
<220> FEATURE:
<223> OTHER INFORMATION: amino acid sequence of target protein sequence

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 2
<211> LENGTH: 29
<212> TYPE: PRT
<213> ORGANISM: Artificial Sequence
<220> FEATURE:
<223> OTHER INFORMATION: amino acid sequence of target protein sequence

<400> SEQUENCE: 2

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25
```

<210> SEQ ID NO 3
<211> LENGTH: 27
<212> TYPE: PRT
<213> ORGANISM: Artificial Sequence
<220> FEATURE:
<223> OTHER INFORMATION: amino acid sequence of target protein sequence

<400> SEQUENCE: 3

Thr Phe Thr Ser Asp Val Ser Ser Tyr Leu Glu Gly Gln Ala Ala Lys
1               5                   10                  15

Glu Phe Ile Ala Trp Leu Val Arg Gly Arg Gly
            20                  25

<210> SEQ ID NO 4
<211> LENGTH: 33
<212> TYPE: PRT
<213> ORGANISM: Artificial Sequence
<220> FEATURE:
<223> OTHER INFORMATION: amino acid sequence of target protein sequence

<400> SEQUENCE: 4

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 5
<211> LENGTH: 29
<212> TYPE: PRT
<213> ORGANISM: Artificial Sequence
<220> FEATURE:
<223> OTHER INFORMATION: amino acid sequence of target protein sequence

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 6
<211> LENGTH: 43
<212> TYPE: PRT
<213> ORGANISM: Artificial Sequence
<220> FEATURE:
<223> OTHER INFORMATION: amino acid sequence of target protein sequence

<400> SEQUENCE: 6

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
        35                  40

<210> SEQ ID NO 7
<211> LENGTH: 453
<212> TYPE: DNA
<213> ORGANISM: Artificial Sequence
<220> FEATURE:
<223> OTHER INFORMATION: nucleotide sequence of nucleic acid encoding
      fusion protein

<400> SEQUENCE: 7
catatgcatc accatcacga agaggcggaa gccgaggccc gtggtaaacg tcacgcagag 60
ggcaccttta cgtctgatgt tagctcttat ctggaaggtc aagcggctaa agagttcatt 120
gcttggttag tgcgcggtcg tggtaaacgt catgctgagg gcacgtttac tagtgatgtg 180
tctagctacc tggaaggcca ggccgcaaaa gagttcatcg cgtggctggt tcgcggtcgt 240
ggtaaacgtc atgctgaagg tacgtttacc agcgatgtta gctcttattt agagggtcag 300
gctgcgaaag aattcatcgc ttggttagtt cgcggtcgtg gcaaacgtca tgctgagggc 360
acctttacga gcgacgtgag tagctacctg gaaggccagg ccgcaaaaga gttcatcgcg 420
tggctggtgc gtggccgcgg ttaatgagga tcc 453

<210> SEQ ID NO 8
<211> LENGTH: 429
<212> TYPE: DNA
<213> ORGANISM: Artificial Sequence
<220> FEATURE:
<223> OTHER INFORMATION: nucleotide sequence of nucleic acid encoding fusion protein

<400> SEQUENCE: 8
catatgcacc atcatcatga ggaagcggag gcggaagcgc gtggcaagcg tgagggcacc 60
ttcaccagcg acgtgagcag ctacctggag ggtcaggcgg cgaaggaatt catcgcgtgg 120
ctggtgcgtg gtcgtggcaa acgtgaaggt acctttacca gcgatgttag cagctatctg 180
gagggccaag cggcgaagga attcattgcg tggctggttc gcggtcgtgg caaacgtgag 240
ggtaccttta ccagcgacgt tagcagctac ctggaaggcc aggcggcgaa agagtttatt 300
gcgtggctgg ttcgtggccg cggtaagcgc gaaggcacct ttaccagcga tgtgagcagc 360
tatctggaag gtcaagcggc gaaagaattt atcgcgtggc tggtgcgcgg tcgtggctaa 420
tgaggatcc 429

<210> SEQ ID NO 9
<211> LENGTH: 405
<212> TYPE: DNA
<213> ORGANISM: Artificial Sequence
<220> FEATURE:
<223> OTHER INFORMATION: nucleotide sequence of nucleic acid encoding fusion protein

<400> SEQUENCE: 9
catatgcatc accatcacga agaggcggaa gccgaggccc gtggtaaacg tacctttacg 60
tctgatgtta gctcttatct ggaaggtcaa gcggctaaag agttcattgc ttggttagtg 120
cgcggtcgtg gtaaacgtac gtttactagt gatgtgtcta gctacctgga aggccaggcc 180
gcaaaagagt tcatcgcgtg gctggttcgc ggtcgtggta aacgtacgtt taccagcgat 240
gttagctctt atttagaggg tcaggctgcg aaagaattca tcgcttggtt agttcgcggt 300
cgtggcaaac gtacctttac gagcgacgtg agtagctacc tggaaggcca ggccgcaaaa 360
gagttcatcg cgtggctggt gcgtggccgc ggttaatgag gatcc 405

<210> SEQ ID NO 10
<211> LENGTH: 486
<212> TYPE: DNA
<213> ORGANISM: Artificial Sequence
<220> FEATURE:
<223> OTHER INFORMATION: nucleotide sequence of nucleic acid encoding fusion protein

<400> SEQUENCE: 10
catatgcatc accatcacga agaggcggaa gccgaggccc gtggtaaacg tcacggtgat 60
ggctctttta gcgacgagat gaatacgatt ctggataact tagcggctcg tgacttcatc 120
aattggctga ttcaaaccaa aatcacggat cgtaaacgtc atggcgacgg tagcttctct 180
gatgaaatga atacgattct ggataactta gcggctcgtg acttcatcaa ttggctgatt 240
caaaccaaaa tcacggatcg taaacgtcat ggcgacggta gcttctctga tgaaatgaat 300
acgattctgg ataacttagc ggctcgtgac ttcatcaatt ggctgattca aaccaaaatc 360
acggatcgta aacgtcatgg cgacggtagc ttctctgatg aaatgaatac gattctggat 420
aacttagcgg ctcgtgactt catcaattgg ctgattcaaa ccaaaatcac ggattaatga 480
ggatcc 486

<210> SEQ ID NO 11
<211> LENGTH: 822
<212> TYPE: DNA
<213> ORGANISM: Artificial Sequence
<220> FEATURE:
<223> OTHER INFORMATION: nucleotide sequence of nucleic acid encoding
fusion protein

<400> SEQUENCE: 11
catatgcatc accatcacga agaggcggaa gccgaggccc gtggtaaacg tcatagccag 60
ggtaccttta ccagtgatta tagcaaatat ctggatagcc gtcgcgcaca ggattttgtg 120
caatggctga tgaatacccg taaacgccat tcacagggta cctttaccag cgattacagc 180
aaatatctgg atagccgtcg cgcacaggat tttgttcagt ggctgatgaa tacccgcaaa 240
cgtcatagcc agggtacctt taccagtgat tatagcaaat atctggattc ccgccgtgcg 300
caggatttcg ttcagtggct gatgaatacc cgcaaacgtc atagccaggg tacctttacc 360
agcgattata gcaaatatct ggatagccgt cgtgcgcagg atttcgttca gtggctgatg 420
aatacccgta aacgccatag ccaaggcacc tttaccagcg attacagcaa atacctggat 480
agccgtcgcg cacaggattt tgttcagtgg ctgatgaata cccgcaaacg tcattcacag 540
ggtaccttta ccagcgatta cagcaaatat ctggatagcc gtcgcgcgca ggattttgtt 600
cagtggctga tgaatacccg caaacgtcat agccagggta cctttaccag cgattatagc 660
aaatatctgg attcccgccg tgcacaggat ttcgttcagt ggctgatgaa tacccgcaaa 720
cgtcatagcc agggtacctt taccagcgat tacagcaaat atctggatag ccgtcgtgcg 780
caggatttcg ttcagtggct gatgaatacc taatgaggat cc 822

<210> SEQ ID NO 12
<211> LENGTH: 606
<212> TYPE: DNA
<213> ORGANISM: Artificial Sequence
<220> FEATURE:
<223> OTHER INFORMATION: nucleotide sequence of nucleic acid encoding
fusion protein

<400> SEQUENCE: 12
catatgcacc atcatcatga ggaagcggag gcggaagcgc gtggcaagcg tagcgacaaa 60
ccggatatgg cggagatcga aaagttcgac aagagcaaac tgaagaaaac cgagacccag 120
gaaaagaacc cgctgccgag caaagagacc atcgagcagg aaaagcaagc gggcgaaagc 180
cgtaaacgta gcgataagcc ggacatggcg gagattgaaa agttcgataa gagcaagctg 240

-continued

```
aagaaaaccg aaacccaaga aaagaacccg ctgcctagca aggaaaccat tgaacaggaa    300

aagcaagcgg gtgaaagccg taagcgtagc gataaaccgg acatggcgga aattgaaaaa    360

tttgataaat ctaagctgaa gaaaaccgag actcaggaaa agaacccgct gccaagcaag    420

gaaaccattg agcaagagaa acaggcgggt gagagccgta aacgttctga taagccggat    480

atggcggaaa tcgagaaatt tgacaaatct aaactgaaga aaaccgaaac tcaggaaaag    540

aacccgctgc ccagcaaaga gaccattgag caggaaaaac aagcgggtga aagctaatga    600

ggatcc                                                               606


<210> SEQ ID NO 13
<211> LENGTH: 146
<212> TYPE: PRT
<213> ORGANISM: Artificial Sequence
<220> FEATURE:
<223> OTHER INFORMATION: sequence of Arg34-GLP-1 (7-37) repeats in
      series connection

<400> SEQUENCE: 13

Met His His His His Glu Glu Ala Glu Ala Glu Ala Arg Gly Lys Arg
1               5                   10                  15

His Ala Glu Gly Thr Phe Thr Ser Asp Val Ser Ser Tyr Leu Glu Gly
            20                  25                  30

Gln Ala Ala Lys Glu Phe Ile Ala Trp Leu Val Arg Gly Arg Gly Lys
        35                  40                  45

Arg His Ala Glu Gly Thr Phe Thr Ser Asp Val Ser Ser Tyr Leu Glu
    50                  55                  60

Gly Gln Ala Ala Lys Glu Phe Ile Ala Trp Leu Val Arg Gly Arg Gly
65                  70                  75                  80

Lys Arg His Ala Glu Gly Thr Phe Thr Ser Asp Val Ser Ser Tyr Leu
                85                  90                  95

Glu Gly Gln Ala Ala Lys Glu Phe Ile Ala Trp Leu Val Arg Gly Arg
            100                 105                 110

Gly Lys Arg His Ala Glu Gly Thr Phe Thr Ser Asp Val Ser Ser Tyr
        115                 120                 125

Leu Glu Gly Gln Ala Ala Lys Glu Phe Ile Ala Trp Leu Val Arg Gly
    130                 135                 140

Arg Gly
145


<210> SEQ ID NO 14
<211> LENGTH: 138
<212> TYPE: PRT
<213> ORGANISM: Artificial Sequence
<220> FEATURE:
<223> OTHER INFORMATION: sequence of Arg34-GLP-1 (9-37) repeats in
      series connection

<400> SEQUENCE: 14

Met His His His His Glu Glu Ala Glu Ala Glu Ala Arg Gly Lys Arg
1               5                   10                  15

Glu Gly Thr Phe Thr Ser Asp Val Ser Ser Tyr Leu Glu Gly Gln Ala
            20                  25                  30

Ala Lys Glu Phe Ile Ala Trp Leu Val Arg Gly Arg Gly Lys Arg Glu
        35                  40                  45

Gly Thr Phe Thr Ser Asp Val Ser Ser Tyr Leu Glu Gly Gln Ala Ala
    50                  55                  60
```

```
Lys Glu Phe Ile Ala Trp Leu Val Arg Gly Arg Gly Lys Arg Glu Gly
65                  70                  75                  80

Thr Phe Thr Ser Asp Val Ser Ser Tyr Leu Glu Gly Gln Ala Ala Lys
                85                  90                  95

Glu Phe Ile Ala Trp Leu Val Arg Gly Arg Gly Lys Arg Glu Gly Thr
            100                 105                 110

Phe Thr Ser Asp Val Ser Ser Tyr Leu Glu Gly Gln Ala Ala Lys Glu
        115                 120                 125

Phe Ile Ala Trp Leu Val Arg Gly Arg Gly
    130                 135
```

<210> SEQ ID NO 15
<211> LENGTH: 130
<212> TYPE: PRT
<213> ORGANISM: Artificial Sequence
<220> FEATURE:
<223> OTHER INFORMATION: sequence of Arg34-GLP-1 (11-37) repeats in series connection

<400> SEQUENCE: 15

```
Met His His His His Glu Glu Ala Glu Ala Glu Ala Arg Gly Lys Arg
1               5                   10                  15

Thr Phe Thr Ser Asp Val Ser Ser Tyr Leu Glu Gly Gln Ala Ala Lys
            20                  25                  30

Glu Phe Ile Ala Trp Leu Val Arg Gly Arg Gly Lys Arg Thr Phe Thr
        35                  40                  45

Ser Asp Val Ser Ser Tyr Leu Glu Gly Gln Ala Ala Lys Glu Phe Ile
    50                  55                  60

Ala Trp Leu Val Arg Gly Arg Gly Lys Arg Thr Phe Thr Ser Asp Val
65                  70                  75                  80

Ser Ser Tyr Leu Glu Gly Gln Ala Ala Lys Glu Phe Ile Ala Trp Leu
                85                  90                  95

Val Arg Gly Arg Gly Lys Arg Thr Phe Thr Ser Asp Val Ser Ser Tyr
            100                 105                 110

Leu Glu Gly Gln Ala Ala Lys Glu Phe Ile Ala Trp Leu Val Arg Gly
        115                 120                 125

Arg Gly
    130
```

<210> SEQ ID NO 16
<211> LENGTH: 157
<212> TYPE: PRT
<213> ORGANISM: Artificial Sequence
<220> FEATURE:
<223> OTHER INFORMATION: sequence of GLP-2 repeats in series connection

<400> SEQUENCE: 16

```
Met His His His His Glu Glu Ala Glu Ala Glu Ala Arg Gly Lys Arg
1               5                   10                  15

His Gly Asp Gly Ser Phe Ser Asp Glu Met Asn Thr Ile Leu Asp Asn
            20                  25                  30

Leu Ala Ala Arg Asp Phe Ile Asn Trp Leu Ile Gln Thr Lys Ile Thr
        35                  40                  45

Asp Arg Lys Arg His Gly Asp Gly Ser Phe Ser Asp Glu Met Asn Thr
    50                  55                  60

Ile Leu Asp Asn Leu Ala Ala Arg Asp Phe Ile Asn Trp Leu Ile Gln
65                  70                  75                  80
```

```
Thr Lys Ile Thr Asp Arg Lys Arg His Gly Asp Gly Ser Phe Ser Asp
                85                  90                  95

Glu Met Asn Thr Ile Leu Asp Asn Leu Ala Ala Arg Asp Phe Ile Asn
            100                 105                 110

Trp Leu Ile Gln Thr Lys Ile Thr Asp Arg Lys Arg His Gly Asp Gly
        115                 120                 125

Ser Phe Ser Asp Glu Met Asn Thr Ile Leu Asp Asn Leu Ala Ala Arg
    130                 135                 140

Asp Phe Ile Asn Trp Leu Ile Gln Thr Lys Ile Thr Asp
145                 150                 155


<210> SEQ ID NO 17
<211> LENGTH: 269
<212> TYPE: PRT
<213> ORGANISM: Artificial Sequence
<220> FEATURE:
<223> OTHER INFORMATION: sequence of Glucagon repeats in series
      connection

<400> SEQUENCE: 17

Met His His His His Glu Glu Ala Glu Ala Glu Ala Arg Gly Lys Arg
1               5                   10                  15

His Ser Gln Gly Thr Phe Thr Ser Asp Tyr Ser Lys Tyr Leu Asp Ser
            20                  25                  30

Arg Arg Ala Gln Asp Phe Val Gln Trp Leu Met Asn Thr Arg Lys Arg
        35                  40                  45

His Ser Gln Gly Thr Phe Thr Ser Asp Tyr Ser Lys Tyr Leu Asp Ser
    50                  55                  60

Arg Arg Ala Gln Asp Phe Val Gln Trp Leu Met Asn Thr Arg Lys Arg
65                  70                  75                  80

His Ser Gln Gly Thr Phe Thr Ser Asp Tyr Ser Lys Tyr Leu Asp Ser
                85                  90                  95

Arg Arg Ala Gln Asp Phe Val Gln Trp Leu Met Asn Thr Arg Lys Arg
            100                 105                 110

His Ser Gln Gly Thr Phe Thr Ser Asp Tyr Ser Lys Tyr Leu Asp Ser
        115                 120                 125

Arg Arg Ala Gln Asp Phe Val Gln Trp Leu Met Asn Thr Arg Lys Arg
    130                 135                 140

His Ser Gln Gly Thr Phe Thr Ser Asp Tyr Ser Lys Tyr Leu Asp Ser
145                 150                 155                 160

Arg Arg Ala Gln Asp Phe Val Gln Trp Leu Met Asn Thr Arg Lys Arg
                165                 170                 175

His Ser Gln Gly Thr Phe Thr Ser Asp Tyr Ser Lys Tyr Leu Asp Ser
            180                 185                 190

Arg Arg Ala Gln Asp Phe Val Gln Trp Leu Met Asn Thr Arg Lys Arg
        195                 200                 205

His Ser Gln Gly Thr Phe Thr Ser Asp Tyr Ser Lys Tyr Leu Asp Ser
    210                 215                 220

Arg Arg Ala Gln Asp Phe Val Gln Trp Leu Met Asn Thr Arg Lys Arg
225                 230                 235                 240

His Ser Gln Gly Thr Phe Thr Ser Asp Tyr Ser Lys Tyr Leu Asp Ser
                245                 250                 255

Arg Arg Ala Gln Asp Phe Val Gln Trp Leu Met Asn Thr
            260                 265


<210> SEQ ID NO 18
```

<211> LENGTH: 197
<212> TYPE: PRT
<213> ORGANISM: Artificial Sequence
<220> FEATURE:
<223> OTHER INFORMATION: sequence of TB4 repeats in series connection

<400> SEQUENCE: 18

Met His His His His Glu Glu Ala Glu Ala Glu Ala Arg Gly Lys Arg
1 5 10 15

Ser Asp Lys Pro Asp Met Ala Glu Ile Glu Lys Phe Asp Lys Ser Lys
20 25 30

Leu Lys Lys Thr Glu Thr Gln Glu Lys Asn Pro Leu Pro Ser Lys Glu
35 40 45

Thr Ile Glu Gln Glu Lys Gln Ala Gly Glu Ser Arg Lys Arg Ser Asp
50 55 60

Lys Pro Asp Met Ala Glu Ile Glu Lys Phe Asp Lys Ser Lys Leu Lys
65 70 75 80

Lys Thr Glu Thr Gln Glu Lys Asn Pro Leu Pro Ser Lys Glu Thr Ile
85 90 95

Glu Gln Glu Lys Gln Ala Gly Glu Ser Arg Lys Arg Ser Asp Lys Pro
100 105 110

Asp Met Ala Glu Ile Glu Lys Phe Asp Lys Ser Lys Leu Lys Lys Thr
115 120 125

Glu Thr Gln Glu Lys Asn Pro Leu Pro Ser Lys Glu Thr Ile Glu Gln
130 135 140

Glu Lys Gln Ala Gly Glu Ser Arg Lys Arg Ser Asp Lys Pro Asp Met
145 150 155 160

Ala Glu Ile Glu Lys Phe Asp Lys Ser Lys Leu Lys Lys Thr Glu Thr
165 170 175

Gln Glu Lys Asn Pro Leu Pro Ser Lys Glu Thr Ile Glu Gln Glu Lys
180 185 190

Gln Ala Gly Glu Ser
195

<210> SEQ ID NO 19
<211> LENGTH: 7
<212> TYPE: PRT
<213> ORGANISM: Artificial Sequence
<220> FEATURE:
<223> OTHER INFORMATION: expression promoting sequence

<400> SEQUENCE: 19

Glu Glu Ala Glu Ala Glu Ala
1 5

<210> SEQ ID NO 20
<211> LENGTH: 9
<212> TYPE: PRT
<213> ORGANISM: Artificial Sequence
<220> FEATURE:
<223> OTHER INFORMATION: expression promoting sequence

<400> SEQUENCE: 20

Glu Glu Ala Glu Ala Glu Ala Gly Gly
1 5

<210> SEQ ID NO 21
<211> LENGTH: 9
<212> TYPE: PRT
<213> ORGANISM: Artificial Sequence
<220> FEATURE:

<223> OTHER INFORMATION: expression promoting sequence

<400> SEQUENCE: 21

```
Glu Glu Ala Glu Ala Glu Ala Arg Gly
1               5
```